United States Patent
Hu et al.

(10) Patent No.: US 11,471,428 B2
(45) Date of Patent: Oct. 18, 2022

(54) METHOD AND PHARMACEUTICAL COMPOSITION FOR TREATING DEPRESSION

(71) Applicant: ZHEJIANG UNIVERSITY, Zhejiang (CN)

(72) Inventors: Hailan Hu, Hangzhou (CN); Yan Yang, Hangzhou (CN); Yihui Cui, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 34 days.

(21) Appl. No.: 16/679,195

(22) Filed: Nov. 9, 2019

(65) Prior Publication Data

US 2020/0069613 A1 Mar. 5, 2020

Related U.S. Application Data

(63) Continuation of application No. PCT/CN2018/086043, filed on May 8, 2018.

(30) Foreign Application Priority Data

| May 9, 2017 | (CN) | .......................... 201710322266.1 |
| May 9, 2017 | (CN) | .......................... 201710322646.5 |
| May 9, 2017 | (CN) | .......................... 201710322647.X |

(51) Int. Cl.
| *A61K 31/135* | (2006.01) |
| *A61P 25/24* | (2006.01) |
| *A61K 31/4015* | (2006.01) |
| *A61K 31/4184* | (2006.01) |

(52) U.S. Cl.
CPC ........ *A61K 31/135* (2013.01); *A61K 31/4015* (2013.01); *A61K 31/4184* (2013.01); *A61P 25/24* (2018.01)

(58) Field of Classification Search
CPC .............................. A61K 31/135; A61P 25/24
See application file for complete search history.

(56) References Cited

U.S. PATENT DOCUMENTS

| 4,694,010 A | 9/1987 | Musacchio |
| 2016/0375000 A1 | 12/2016 | Kim et al. |

FOREIGN PATENT DOCUMENTS

| CN | 102512682 A | 6/2012 | |
| CN | 106562952 A | 4/2017 | |
| WO | 2007/111880 A | 10/2007 | |
| WO | WO-2007111880 A2 * | 10/2007 | ........... A61K 31/137 |

OTHER PUBLICATIONS

Zeynep, AA: Adeboye, A.,"NMDA Receptor Antagonists for Treatment of Depression" Pharmaceuticals, vol. 6, Apr. 3, 2013 (Apr. 3, 2013), ISSN: 1424-8247, pp. 480-499.
Kraus RL et al., "Trazodone inhibits T-type calcium channels", Neuropharmacology. Aug. 2007;53(2):308-17. doi: 10.1016/j.neuropharm.2007.05.011. Epub May 26, 2007, PMID: 17610910 DOI: 10.1016/j.neuropharm.2007.05.011.
First OA of Chinese Patent Office for Chinese Application No. 201710322647.X, mailed Jul. 29, 2020.
Richard L Kraus et al: Trazodone inhibits T-type calcium channels, Neuropharmacology, Pergamon Press, Oxford, GB, vol. 53, No. 2, Aug. 6, 2007 (Aug. 6, 2007), pp. 308-317, XP022188033, ISSN: 0028-3908, DOI: 10.1016/J.NEUROPHARM.2007.05.011.
Henrike Hartung et al: "High-frequency stimulation of the subthalamic nucleus modulates neuronal activity in the lateral habenula nucleus", European Journal of Neuroscience., vo 1 • 44, No. 9, Oct. 13, 2016 (Oct. 13, 2016), pp. 2698-2707, XP055733278, GB ISSN: 0953-816X, DOI: 10.1111/ejn.13397.
Supplementary European Search Report of the Application No. EP 18798176.6, mailed 2021-01-18.
Cao, Qiuyun , "The Clinical Features and Treatment of Late-Onset Depression", Chinese Journal of Brain Diseases and Rehabilitation,Jun. 30, 2015 (Jun. 30, 2015), ISSN: 2095-123X, pp. 141-144.
Yang, Hongbo; Zhang, Jichuan, "Research Progress on Effect of Lateral Habenular Nucleus in Depression"; Mar. 31, 2016 (Mar. 31, 2016), ISSN: 1005-9202, pp. 1246-1248, (Chinese Journal of Gerontology), non-official translation.
International Search Report in the international application No. PCT/CN2018/086043, dated Aug. 10, 2018.
English translation of the Written Opinion of the International Search Authority in the international application No. PCT/CN2018/086043, dated Aug. 10, 2018.

* cited by examiner

*Primary Examiner* — Kevin E Weddington
(74) *Attorney, Agent, or Firm* — Pattao, LLC; Junjie Feng

(57) ABSTRACT

A method for treating a subject with depression characterized by having an increased burst firing in neurons of a lateral habenula in the subject is provided. The method includes a step of administering to the subject a pharmaceutical composition capable of inhibiting the burst firing in the lateral habenula of the subject. The pharmaceutical composition includes one or more active pharmaceutical agents, which can suppress the burst firing in the lateral habenula of the subject and can include at least one of an N-methyl-D-aspartate receptor (NMDAR) inhibitor or a T-type calcium channel inhibitor. The pharmaceutical composition can be in a formulation allowing for local administration to the lateral habenula of the subject, or can be in a formulation configured for systemic administration to the subject. A method for testing a test substance for an antidepressive effect is also provided.

11 Claims, 23 Drawing Sheets

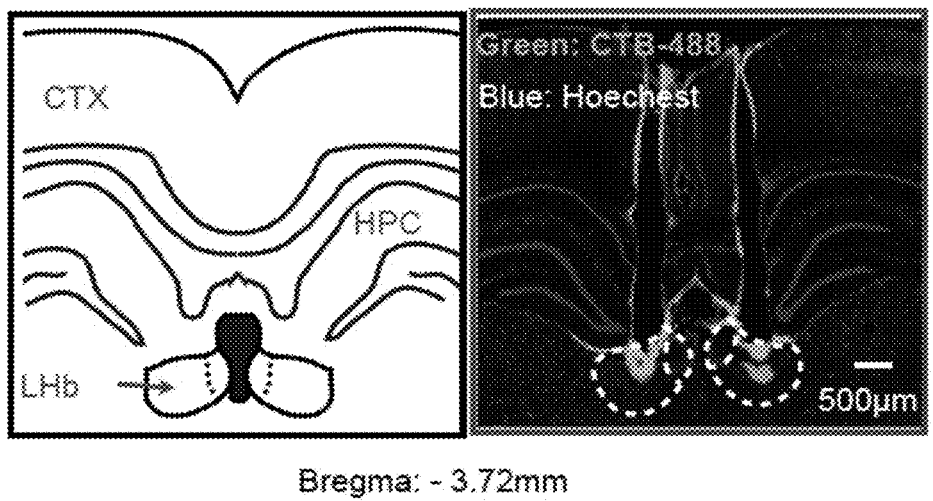
Bregma: -3.72mm
FIG. 1A
● cLH+sal  ● cLH+ket
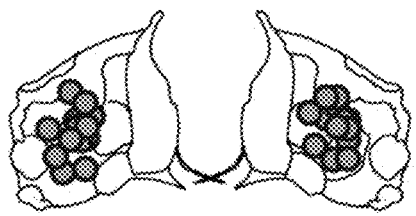
FIG. 1B
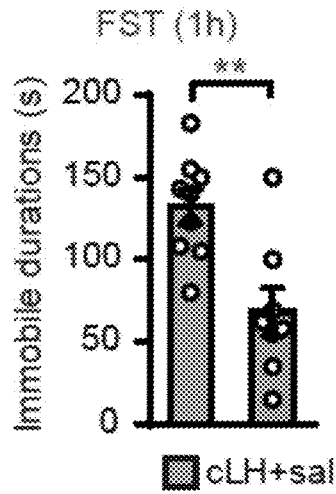 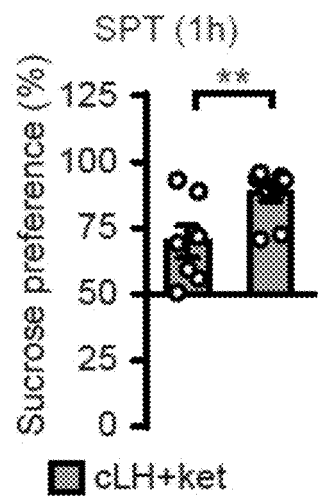
FIG. 1C      FIG. 1D

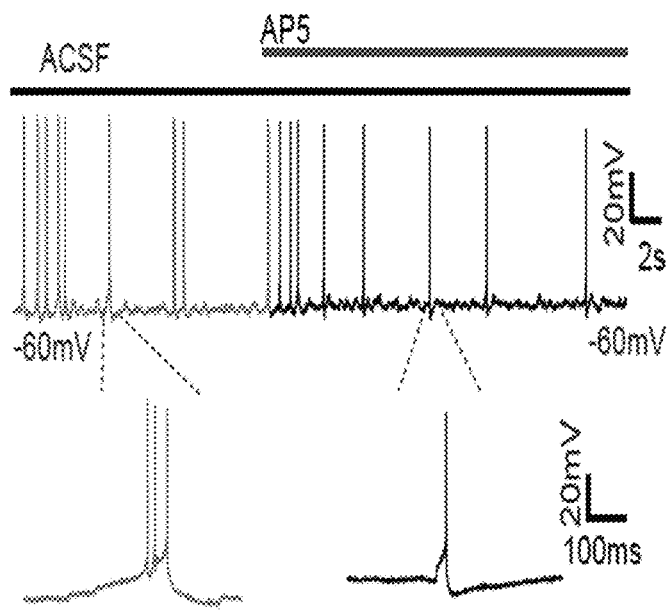
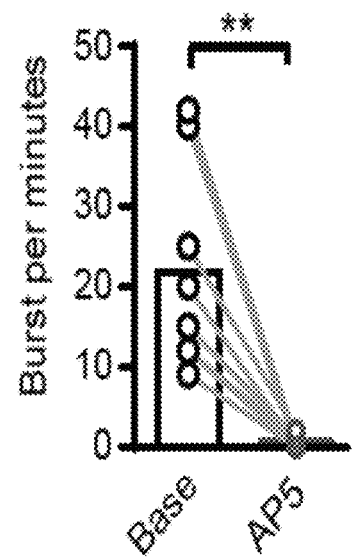
FIG. 4E   FIG. 4F
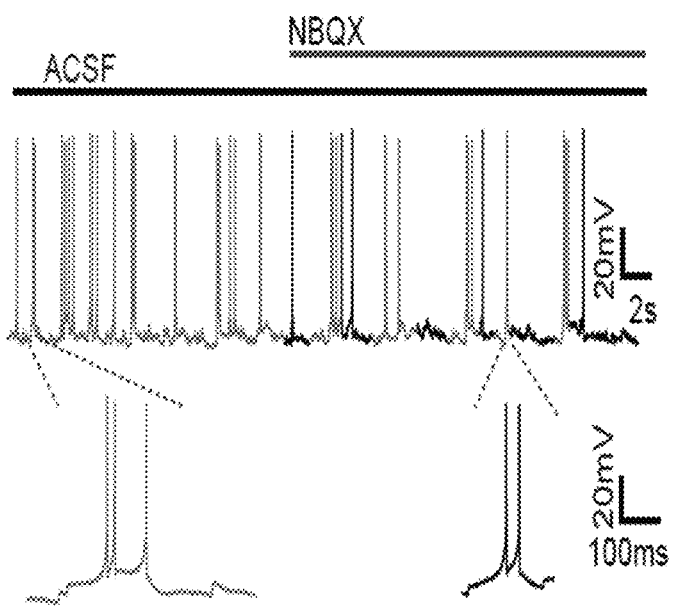
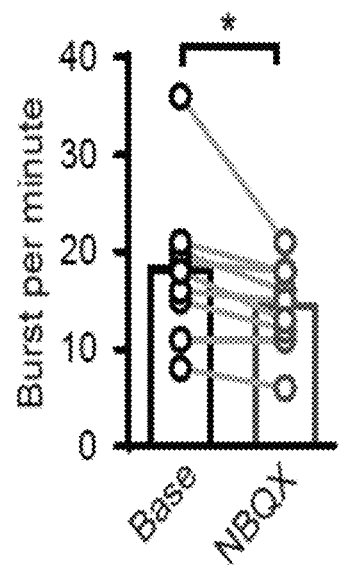
FIG. 4G   FIG. 4H

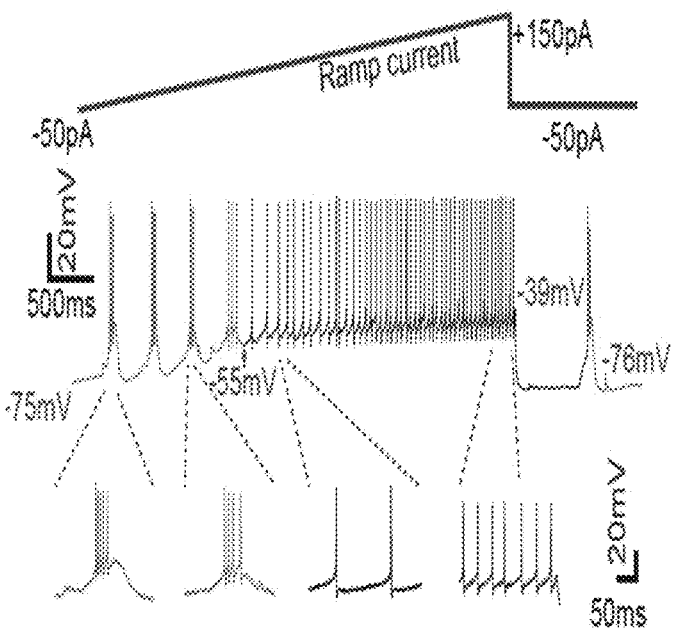
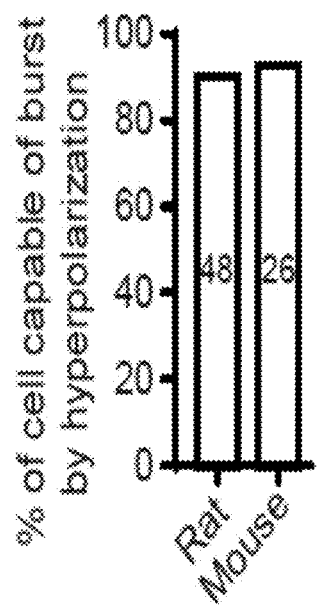
FIG. 5A  FIG. 5B
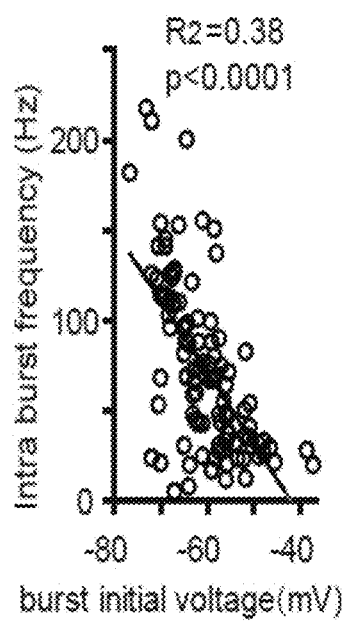
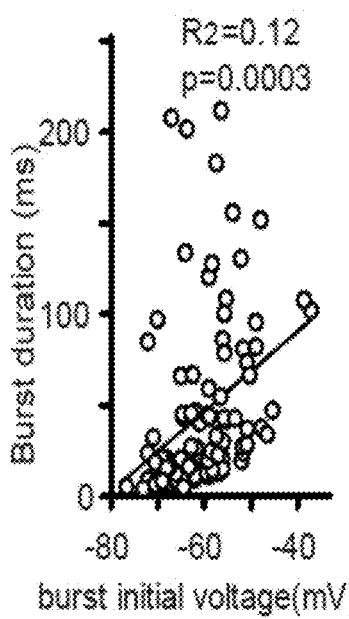
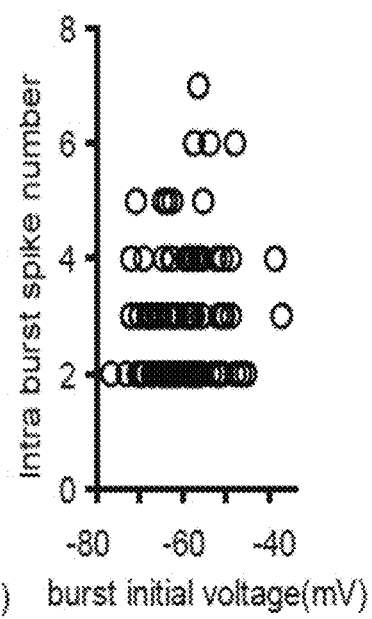
FIG. 5C  FIG. 5D  FIG. 5E

FIG. 6C      FIG. 7A

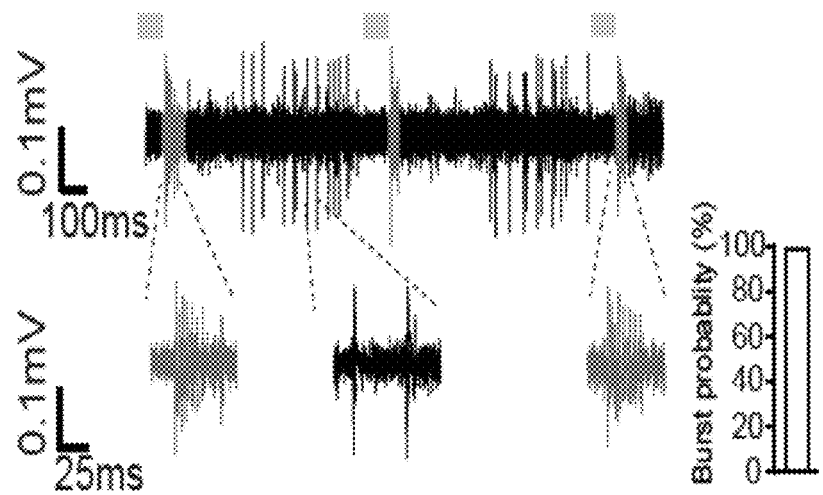
FIG. 7C
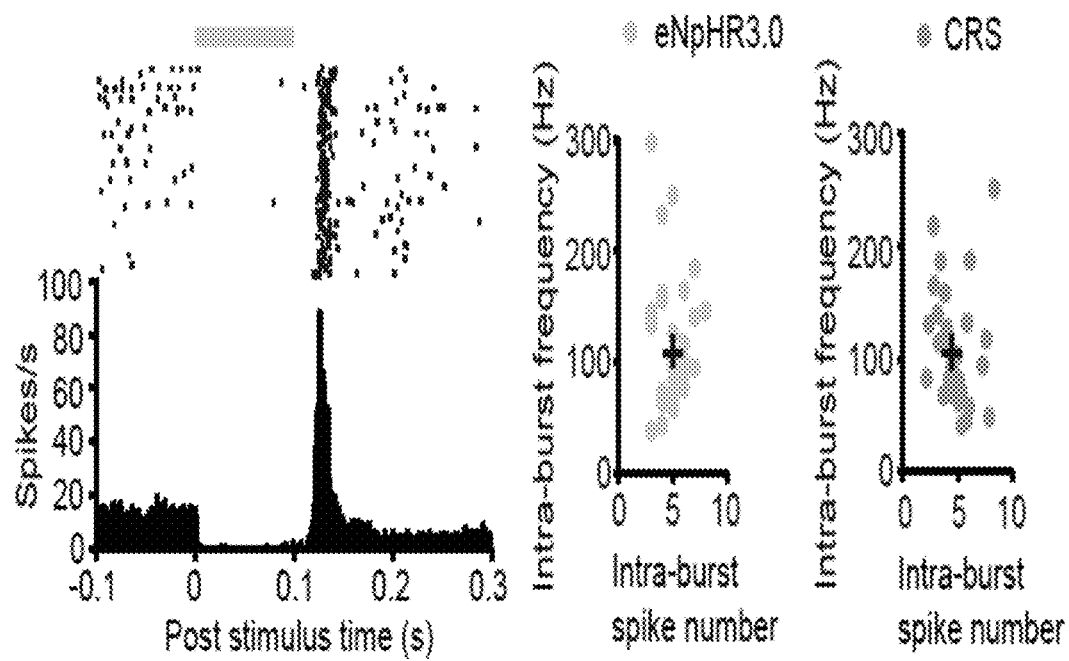
FIG. 7D  FIG. 7E

METHOD AND PHARMACEUTICAL COMPOSITION FOR TREATING DEPRESSION

CROSS-REFERENCE TO RELATED PATENT APPLICATIONS

The present application is a continuation of International Patent Application No. PCT/CN2018/086043 filed May 8, 2018, which claims priority to Chinese Patent Application No. 201710322647.X filed May 9, 2017, Chinese Patent Application No. 201710322266.1 filed May 9, 2017, and Chinese Patent Application No. 201710322646.5 filed May 9, 2017, which are hereby incorporated into the present application by reference in their entirety.

FIELD OF THE INVENTION

The present disclosure relates to the field of disease therapy and pharmacy, and in particular, provides a method for treating depression and pharmaceutical compositions for treating depression and a method for manufacturing it.

BACKGROUND

Depression, sometimes also known as major depressive disorder, has a high incidence in the population. If left untreated, a depression patient may be debilitating emotionally and physically. Based on the definition and description by the US National Institute of Mental Health, depression can include a range of symptoms, including "persistently sad, anxious, or empty" moods; senses of hopelessness, pessimism, guilt, worthlessness, or helplessness, losses of interests or pleasure in hobbies and activities once enjoyed; reduced energy and fatigue; difficulties in concentrating, memorizing, and decision-making; hyperactivity, and irritability, etc.

Lateral habenula (LHb) is a lateral part of habenula which, together with the pineal gland, forms the epithalamus. LHb is the primary tissue that communicatively connects the limbic forebrain with the midbrain. In recent years, it has been found that LHb links and regulates the dopaminergic and serotonergic nerve fibers, participating in a wide range of physiological activities and affecting body functions, and thus having associations with a variety of mental states and psychiatric disorders, such as drug addiction, reward and avoidance, pain, and sleep, etc.

Evidence from human studies and animal models has surged to associate LHb with the occurrence of depression. Studies show that in rats with both acute learned helplessness (aLH) and congenital learned helplessness (cLH) depression, VTA-projecting habenula neurons exhibit significantly elevated frequency in the micro-exciting post-synaptic current (mEPSC) compared with normal rats, indicating that the enhanced synaptic activity associated with depression may be mediated by the synaptic plasticity (Li et al., 2011). In normal state, LHb has relatively weak inhibition on VTA and DRN. In depressive state, stress causes a significant upregulation of BCaMKII level, which leads to increased membrane trafficking of GluR1, increased synaptic efficacy and spike output of LHb neurons. As a result, the LHb inhibition onto VTA and DRN are enhanced, causing anhedonia and behavioral despair (Li et al., 2013).

There are already some commonly used antidepressants in the field, but these drugs usually take effect after a long period of time. Almost all known existing antidepressants in the field typically take a week to several weeks to be capable of exerting antidepressant effects. For example, the commonly used 5-HT reuptake inhibitors (SSRI) are usually effective in 2-3 weeks; 5-HT and serotonin and norepinephrine reuptake inhibitors are usually only effective after 1 week. Moreover, the pathological mechanism leading to depression has not yet been fully recognized. There is a need in the field for new methods and new drugs capable of treating depression, which are more fast-acting or have safer effective dosages.

SUMMARY OF THE INVENTION

The present application, for the first time and in an unexpected manner, discloses that burst firings in neurons of the lateral habenula have an important role in the onset of depression, and identifies key factors affecting the burst firings in the lateral habenula, thereby providing a method and medicament for treating (i.e. suppressing) depression by inhibiting burst firings in lateral habenula, and in more particular providing a method and medicament for rapidly treating (i.e. suppressing) depression (Yang et al. 2018).

In particular, the present disclosure provides methods for treating depression in subjects by inhibiting burst firings in lateral habenula in said subject. The present disclosure further provides a pharmaceutical agent capable of inhibiting burst firing in lateral habenula to treat depression, especially those that act upon the lateral habenula. The present disclosure also provides a pharmaceutical composition for treating depression, especially those that act upon the lateral habenula, which comprise(s) one or more pharmaceutical agents capable of inhibiting burst firing in lateral habenula. Herein, the one or more pharmaceutical agents capable of inhibiting burst firing in lateral habenula can be regarded as pharmaceutically or therapeutically active agent(s) or active ingredients in the pharmaceutical composition for treating depression.

In a first aspect, the present disclosure provides a method for treating a depression having an increased burst firing in neurons of a lateral habenula in a subject. The method includes a step of administering to the subject a pharmaceutical composition capable of inhibiting the burst firing in the lateral habenula of the subject.

According to different embodiments of the method, the pharmaceutical composition is capable of inhibiting the burst firing by reducing at least one of a number of burst firing cells in the lateral habenula, a ratio of burst firing cells among neurons in the lateral habenula, a probability of the burst firing, a frequency of the burst firing, an amplitude of the burst firing, a duration of the burst firing, or a spike number per burst.

Furthermore, according to some embodiments of the method, the pharmaceutical composition allows for rapidly relieving symptoms of depression, and as such, renders the method for rapidly relieving depression.

In the method, the pharmaceutical composition can be optionally administered locally. In other words, in the method, the step of administering to the subject a pharmaceutical composition capable of inhibiting the burst firing in the lateral habenula of the subject comprises a step of administering the pharmaceutical composition locally to the lateral habenula of the subject.

Herein, according to some embodiments of the method, the pharmaceutical composition includes an N-methyl-D-aspartate receptor (NMDAR) inhibitor, which is selected from a competitive NMDA receptor inhibitor, a non-competitive NMDA receptor inhibitor, an uncompetitive NMDA receptor channel blocker, a glycine binding site inhibitor, or an NMDAR antagonist at unknown site.

According to some other embodiments of the method, the pharmaceutical composition includes a T-type calcium channel inhibitor, selected from mibefradil, ethosuximide, methsuximide, hydantoin, zonisamide, sodium valproate, phenytoin, phenytoin, sipatrigine, a piperazine analogue, a piperidine analogue, TTA-P1, TTA-P2, quinazolinone, pimozide, trimethadione, dimethadione, TTA-Q4, or ML218.

According to yet some other embodiments of the method, the pharmaceutical composition a combination of an N-methyl-D-aspartate receptor (NMDAR) inhibitor and a T-type calcium channel inhibitor. Herein optionally, the N-methyl-D-aspartate receptor (NMDAR) inhibitor is ketamine or AP5; and the T-type calcium channel inhibitor is ethosuximide or mibefradil.

Furthermore, in the method, the pharmaceutical composition can be optionally administered to the subject in systemic manner. In other words, in the method, the step of administering to the subject a pharmaceutical composition capable of inhibiting the burst firing in the lateral habenula of the subject comprises a step of administering the pharmaceutical composition systemically to the subject.

Herein, according to some embodiments of the method, the pharmaceutical composition includes at least one of an N-methyl-D-aspartate receptor (NMDAR) inhibitor capable of crossing a blood-brain barrier or a T-type calcium channel inhibitor capable of crossing the blood-brain barrier.

Optionally, the pharmaceutical composition includes an N-methyl-D-aspartate receptor (NMDAR) inhibitor and a T-type calcium channel inhibitor. The N-methyl-D-aspartate receptor (NMDAR) inhibitor can be ketamine; and the T-type calcium channel inhibitor can be ethosuximide or methsuximide.

According to some embodiments of the method, the pharmaceutical composition does not inhibit tonic firing in the lateral habenula of the subject.

In a second aspect, the present disclosure further provides a pharmaceutical composition for treating a depression having an increased burst firing in neurons of a lateral habenula in a subject. The pharmaceutical composition contains one or more active pharmaceutical agents capable of inhibiting the burst firing in the lateral habenula of the subject. As such, the pharmaceutical composition disclosed herein can be used in the method for treating a depression having an increased burst firing in neurons of a lateral habenula in a subject, as described above.

According to some embodiments of the pharmaceutical composition, the one or more active pharmaceutical agents comprise at least one of an N-methyl-D-aspartate receptor (NMDAR) inhibitor or a T-type calcium channel inhibitor.

Optionally, each of the one or more active pharmaceutical agents is capable of crossing a blood-brain barrier of the subject such that the pharmaceutical composition is in a formulation allowing for systemic administration to the subject.

As such, according to some embodiments of the pharmaceutical composition, the one or more active pharmaceutical agents include an N-methyl-D-aspartate receptor (NMDAR) inhibitor and a T-type calcium channel inhibitor. Herein optionally, the N-methyl-D-aspartate receptor (NMDAR) inhibitor is ketamine; and the T-type calcium channel inhibitor is ethosuximide or methsuximide.

Further optionally, the pharmaceutical composition is in a formulation configured for local administration to the lateral habenula of the subject.

As such, according to some embodiments of the pharmaceutical composition, the one or more active pharmaceutical agents include an N-methyl-D-aspartate receptor (NMDAR) inhibitor, selected from a competitive NMDA receptor inhibitor, a non-competitive NMDA receptor inhibitor, an uncompetitive NMDA receptor channel blocker, or a glycine binding site inhibitor, or an NMDAR antagonist at unknown site.

According to some other embodiments of the pharmaceutical composition, the one or more active pharmaceutical agents include a T-type calcium channel inhibitor, selected from mibefradil, ethosuximide, methsuximide, hydantoin, zonisamide, sodium valproate, phenytoin, phenytoin, sipatrigine, a piperazine analogue, a piperidine analogue, TTA-P1, TTA-P2, quinazolinone, pimozide, trimethadione, dimethadione, TTA-Q4, or ML218.

According to yet some other embodiments of the pharmaceutical composition, the one or more active pharmaceutical agents comprise a combination of an N-methyl-D-aspartate receptor (NMDAR) inhibitor and a T-type calcium channel inhibitor. Herein, optionally, the N-methyl-D-aspartate receptor (NMDAR) inhibitor can be ketamine or APS; and the T-type calcium channel inhibitor can be ethosuximide or mibefradil.

In a third aspect, the present disclosure further provides a method for testing a test substance for an antidepressive effect. If a plurality of test substances are to be tested, the method provided herein can substantially be an approach for screening the plurality of test substances to identify promising drug candidates that have antidepressant effects. The method comprises the following steps:

(1) providing a testing model which is characterized by electrophysiologically having an increased burst firing in lateral habenula (LHb) neurons contained therein;

(2) administering the test substance to the testing model;

(3) examining an electrophysiological activity of the LHb neurons in the testing model; and (4) determining, if there is a reduction of the burst firing, that the test substance is an antidepressant candidate having the antidepressive effect.

According to some embodiments of the method, the testing model is an LHb in vitro model, which can be an LHb cell model or an LHb tissue model. Herein the LHb cell model can be an in vitro cell culture system that mimics LHb tissues in the brain of a subject. The LHb tissue model can contain an LHb brain piece or brain slice that is isolated from a subject. Herein the subject can be a mammal subject such as a rat, a mouse, a monkey, etc., or can be a human.

Herein optionally, the LHb neurons can be configured to show spontaneous burst firing, or to show an increased burst firing in an inducible manner.

According to some specific embodiments of the method described herein, the LHb neurons are induced to show an increased burst firing by hyperpolarization current injection.

According to some other specific embodiments, the LHb neurons overexpress an opsin, and are configured to inducibly show an increased burst firing upon eliciting by an enabling light signal corresponding to the opsin. Herein, optionally, the opsin can be an inhibitory opsin eNpHR3.0, and the corresponding enabling light signal comprises yellow light pulses (e.g. 450-650 nm; 0.5-5 Hz). Alternatively, the opsin can be an excitatory opsin oChief, and the corresponding enabling light signal comprises high frequency blue light pulses (e.g. 350-550 nm; 20-100 Hz).

According to some other embodiments of the method, the testing model is an animal model, which can be a depressive animal model. Two non-limiting examples of the depressive animal model include a congenitally learned helpless (cLH) rat model or a chronic restraint stress (CRS) mouse model. Other such models are also possible.

Optionally, the animal model can be engineered to have an inducible burst firing in the LHb neurons. As such, the animal model can be engineered to overexpress an opsin in the LHb neurons, wherein the LHb neurons are configured to inducibly show an increased burst firing upon eliciting by an enabling light signal to the LHb neurons. Optionally herein, the opsin can comprise at least one of an inhibitory opsin eNpHR3.0 with its corresponding enabling light signal comprising yellow light pulses (e.g. 450-650 nm; 0.5-5 Hz), or an excitatory opsin oChief with its corresponding enabling light signal comprising high frequency blue light pulses (e.g. 350-550 nm; 20-100 Hz).

In any one of the embodiments of the method as described above, the reduction of the burst firing can comprise a reduction of at least one of a number of burst firing cells in the lateral habenula, a ratio of burst firing cells among neurons in the lateral habenula, a probability of the burst firing, a frequency of the burst firing, an amplitude of the burst firing, a duration of the burst firing, or a spike number per burst.

In the method, the step (3) examining an electrophysiological activity of the LHb neurons in the testing model can optionally comprise performing a whole cell patch-clamp recording in the LHb cell model or in the LHb tissue model, if the testing model is an LHb in vitro model; or can optionally comprise performing an in vivo multi-tetrode recording in the LHb of the animal model, if the testing model is an animal model.

In embodiments of the method where the testing model is an animal model, the step (2) administering the test substance to the testing model can optionally comprise: administering the test substance systemically to the animal model. Optionally, the step (2) can comprise: administering the test substance locally to the LHb of animal model by means of, for example, cannulation.

In any embodiment of the method described herein, in the step (4): determining, if there is a reduction of the burst firing, that the test substance is an antidepressant candidate having the antidepressive effect, the criterion for judging that "there is a reduction of the burst firing" can be that the post-treatment burst firing activity of the LHb neurons in the test sample is reduced compared with the pre-treatment burst firing activity of the LHb neurons, and the difference (i.e. the reduction of the burst firing) is more than a preset threshold, which can be, for example, 10-100%. In another manner, the criterion for judging that "there is a reduction of the burst firing" can be that the post-treatment burst firing activity of the LHb neurons in the test sample is reduced compared with the pre-treatment burst firing activity of the LHb neurons, and the difference (i.e. the reduction of the burst firing) is statistically significant for a given P-value, which can be for example, $\leq 0.05$, but can be set as a different value depending on practical needs. In yet another manner, the testing of the test substance can involve the use of control substance, and the criterion for judging that "there is a reduction of the burst firing" can accordingly involve a comparison between the test substance and the control substance, and specifically may involve the judgement whether there is a statistically significant (e.g. $P \leq 0.05$) difference between the two groups of substance-induced reduction of the burst firing activity of LHb neurons, i.e. whether the reduction of the burst firing activity of LHb neurons in test group (i.e. the group using the test substance) is statistically significant (e.g. $P \leq 0.05$) more than the reduction of the burst firing activity of LHb neurons in group (i.e. the group using the control substance). Herein the control substance can be blank control substance, such as saline, but can also be other substances such as ketamine and there is no limitation herein.

In any of the manners for the antidepressant-screening method as mentioned above, the "reduction of the burst firing" in the LHb neurons can include one or more of the following: decrease of a number of burst firing cells or a ratio of burst firing cells among neurons in the lateral habenula, decrease of the probability of burst firings (i.e. decreasing the probability of generation of burst firing upon induction), decrease of the frequency of burst firing (i.e. reducing the amount of burst firing), decrease of the bursting amplitude, decrease of spike number per burst (i.e., reducing the number of intra-bursting spikes), decrease of the duration of bursts (i.e. bursting duration).

The term "subject", or "subjects", as referred to throughout the disclosure who receives the methods and medicaments (pharmaceutical compositions) as disclosed in the present disclosure can include subjects that are diagnosed with depression. The subject to be treated can be a mammal, including a human or a non-human primate such as a monkey. The mammal can be other animals such as rats, mice, rabbits, pigs, dogs, and the like. The mammal can be a domestic animal such as a cat or a dog.

The term "burst", or "burst firing", as referred to throughout the disclosure, is defined as a firing pattern in neurons that has two or more spontaneous bursts, or spikes of plateau potentials (short as spikes hereafter) in each time of firing (i.e. each burst).

The term "inhibiting burst firing", "inhibition of burst firing", "inhibiting burst", "inhibition of burst", or alike, is referred to as inhibiting level of neuronal burst firing, which can include: decreasing the number of burst firing cells or reducing the ratio of burst firing cells among neurons in the lateral habenula, decreasing the probability of burst firings (i.e. decreasing the probability of generation of burst firing upon induction), decreasing the frequency of burst firing (i.e. reducing the amount of burst firing), reducing the bursting amplitude, reducing spike number per burst (i.e., reducing the number of intra-bursting spikes), and/or reducing the duration of bursts (i.e. bursting duration).

The term "tonic firing" is referred to as a neuronal firing pattern with only one spike in each burst.

The term "pharmaceutical agent", or "therapeutic agent", "reagent", or alike, that is capable of inhibiting burst firing in the lateral habenula can be a compound, a formulation, or a combination/mix that is capable of pharmaceutically or therapeutically inhibiting burst firing, and can as well include an agent or a reagent used in a method for inhibiting burst firing which shall also include a surgical method. The pharmaceutical agent can be a small molecule compound or a formulation thereof, and can also be a pharmaceutically active macromolecule such as a protein or a nucleic acid which can, for example, be an antagonist such as an antibody that binds to a protein in the burst firing-related physiological pathway, or can be a nucleic acid that affects the expression level of such a protein.

As used herein and throughout the disclosure, the term "treatment" can be interpreted to include a process or an outcome thereof that ameliorates, palliates, decreases or prevents the symptoms associated with depression; a process or an outcome thereof that improves the symptoms associated with depression; a process or an outcome thereof that normalizes body functions in diseases or disorders that result in impairment of the specific body functions; or a process or an outcome thereof that elicits an improvement in one or more of the clinically measured parameters of the disease. In one embodiment, a treatment objective is to prevent or slow down (i.e. lessen) an undesired physiological condition, disorder or disease, or to obtain a beneficial or desired result. Herein the result can be, e.g., medical, physiological, clinical, physical therapy, occupational therapy, and subjective to a health care worker or to a patient; or can be interpreted in the field as a parameter for "quality of life" or for "activity of daily living". For the purposes of this disclosure, the "beneficial or desired result" can comprise, but are not limited to, alleviation of symptoms; diminution/diminishment of the extent of the condition, disorder or disease; stabilization (i.e., not worsening) of the state of the condition, disorder or disease; delay in onset or slowing of the progression of the condition, disorder or disease; amelioration or palliation of the condition, disorder or disease; and remission (partially or totally), whether detectable or undetectable; or enhancement or improvement of the condition, disorder or disease. In one embodiment, treatment includes eliciting a clinically significant response without excessive levels of side effects. In another embodiment, treatment also includes prolonged survival as compared to expected survival if not receiving treatment. In yet another embodiment, treatment is referred to as the administration of a medicine, or the application of a medical procedure, to a patient. As used herein, treatment can comprise prevention or curing of a weakness or a disease of a patient, or can comprise amelioration of the clinical condition of the patient, including a reduced duration or severity of an illness, an improved quality of life of the patient, or a prolonged survival of the patient.

The terms "systemic administration" (or similarly "systemically", "in a systemic manner", or alike) and "local administration" (or similarly "locally", "in a local manner", or alike), as used throughout the disclosure, are in accordance with the convention in the pharmaceutical field, and are referred to as two different routes of administration of a medication or a substance of interest to a subject. The "systemic administration" is typically a route of administration whereby the medication or the substance of interest, upon administration to the subject, enters into the circulatory system so that the entire body is affected. As opposed to the "systemic administration", the "local administration" is substantially equivalent to delivering the medication or the substance of interest almost directly to the site of action (as in this case, the lateral habenula of the subject), typically accompanied with a reduced risk for systemic side effects.

According to one embodiment of the present disclosure, in the method and the pharmaceutical agent for treating depression in a subject by inhibiting burst in lateral habenula or in the pharmaceutical composition for treating depression as provided herein, the pharmaceutical agent capable of inhibiting burst firing in the lateral habenula is a N-methyl-D-aspartate receptor inhibitor.

N-methyl-D-aspartate (NMDA) is an excitatory amino acid (EAA), which is essentially an excitatory neurotransmitter of the central nervous system. The N-methyl-D-aspartate receptor (short as "NMDA receptor" or NMDAR) is an ionic receptor involved in excitatory synaptic transmission. Modulation of NMDA receptors modulates glutamatergic neurotransmitter mediated neurological effects.

Herein, the N-methyl-D-aspartate receptor inhibitors which can be used in the present disclosure include, but are not limited to:

1) competitive NMDA receptor inhibitors (i.e. inhibitors that compete with glutamate binding sites), such as AP5, AP7, CPPene, and Selfotel;
2) non-competitive NMDA receptor inhibitors (i.e. inhibitors that block allosteric binding sites), such as Aptiganel, ketamine, memantine, Huperzine A, Ibogaine, HU-211, Gabapentin, and PD-137889;
3) uncompetitive NMDA receptor channel blockers (i.e. channel blocker), such as Amantadine, Atomoxetine, AZD6765, Dextromethorphan, memantine hydrochloride, and MK801 (Dizocilpine);
4) glycine binding site inhibitors, such as TK-40, and kynurenic acid; or
5) NMDAR antagonists at unknown site, such as $N_2O$.

Among the above mentioned NMDAR inhibitors, those that are capable of crossing a blood-brain barrier or show at least certain level of blood-brain barrier permeability include AP7 (observed but at a low level), CPPene, Selfotel, Aptiganel, ketamine, memantine, Huperzine A, Ibogaine, HU-211, PD-137889, Amantadine, Atomoxetine, AZD6765, Dextromethorphan, memantine hydrochloride, MK801 (Dizocilpine), and kynurenic acid. These NMDAR inhibitors thus are suitable for both systemic or local administration to the subject. On the other hand, AP5 and Gabapentin do not have blood-brain barrier permeability, and they are thus suitable for only local (but not systemic) administration to the lateral habenula of a subject.

According to another embodiment of the present disclosure, in the method and the pharmaceutical agent for treating depression in a subject by inhibiting burst in lateral habenula or in the pharmaceutical composition for treating depression as provided herein, said pharmaceutical agent capable of inhibiting burst firing in the lateral habenula is a T-type calcium channel inhibitor.

A T-type calcium channel is also known as transient calcium channel, or low voltage activate calcium channel. The T-type calcium channel plays an important role in modulating excitations in central and peripheral nervous system. In vertebrates, T-type calcium channel consists of three different α1 subunit genes: CACNA1G, CACNA1H and CACAN1I, encoding α1G, α1H and α1I respectively, which respectively form three subtypes of T-type calcium channels: Cav3.1, Cav3.2, and Cav3.3. A T-type calcium channel is typically a tetramer protein, with each monomer (i.e. α1 subunit) containing four homologous domains. The pore of the channel is composed of the four homologous domains. Pore helices and the terminal of extracellular S6 fraction connect each other to thereby form a selective filter for calcium ions. A positive-charged amino acid residue is present every third amino acid in each S4 fraction of the homologous domain, thereby constituting the channel voltage sensor which controls the switch-on or switch-off of the channel when the membrane potential changes.

Herein, the T-type calcium channel inhibitors which can be used in the present disclosure include, but are not limited to: succinimides (such as ethosuximide and methsuximide), hydantoins, zonisamide, sodium valproate, phenytoin, mibefradil, phenytoin, sipatrigine, piperazine analogues (such as Flunarizine and Z941), piperidine analogues (such as Z944 or fluoropiperidine), TTA-P1, TTA-P2, quinazolinone, pimozide, trimethadione or dimethadione, TTA-Q4, and ML218, etc.

Among the T-type calcium channel inhibitors, each of ethosuximide, methsuximide, hydantoins, zonisamide, sodium valproate, phenytoin, sipatrigine, pimozide, trimethadione or dimethadione and ML218 shows at least some level of blood-brain barrier permeability, and is thus suitable for both systemic and local administration. Mibefradil has no blood-brain barrier permeability, and is thus suitable for only local (but not systemic) administration to the lateral habenula of a subject. The blood-brain barrier permeability of other such inhibitors remains to be determined.

According to yet another embodiment of the present disclosure, in the method and the pharmaceutical agent for treating depression in a subject by inhibiting burst in lateral habenula or in the pharmaceutical composition for treating depression as provided herein, said pharmaceutical agent inhibiting burst in lateral habenula comprises a combination of N-methyl-D-aspartate receptor inhibitor and a T-type calcium channel inhibitor.

The present disclosure provides a method for treating depression in a subject, which comprises administering a combination of component a) N-methyl-D-aspartate receptor (NMDAR) inhibitor, and component b) T-type calcium channel (T-VSCC) inhibitor to said subject.

The present disclosure also provides a pharmaceutical composition for treating depression, which comprises: component a) N-methyl-D-aspartate receptor (NMDAR) inhibitor, and component b) T-type calcium channel (T-VSCC) inhibitor.

According to some embodiments of the present disclosure, in the method or pharmaceutical composition for treating depression, the therapeutically effective amount of at least one of component a) and component b) administered to the subject is less than the therapeutically effective amount thereof when administered in the absence of the other component. According to some other embodiments of the present disclosure, the therapeutically effective amount of both of component a) and component b) administered to the subject is less than the therapeutically effective amount thereof when administered in the absence of the other component.

According to some embodiments of the present disclosure, in the method or pharmaceutical composition for treating depression, the therapeutically effective amount of at least one, and especially both of component a) and component b) administered to the subject, especially the therapeutically effective amount of both of the component a) and component b), is at least 5% less, at least 10% less, at least 25% less, at least 50% less, at least 60% less, at least 70% less, at least 80% less, or at least 90% less than the therapeutically effective amount thereof when administered in the absence of the other component. According to some embodiments, the therapeutically effective amount of at least one of component a) and component b) administered to the subject, is 5-90% less, 10-90% less, 25-90% less, or 50-90% less than the therapeutically effective amount thereof when administered in the absence of the other component.

For example, in the method or pharmaceutical composition for treating depression disclosed herein, the therapeutically effective amount of an NMDAR inhibitor is at least 5% less, at least 10% less, at least 25% less, at least 50% less, at least 60% less, at least 70% less, at least 80% less, or at least 90% less than the therapeutically effective amount of the NMDAR inhibitor when administered in the absence of the T-VSCC inhibitor. That is, in the pharmaceutical composition provided herein, the dosage of NMDAR inhibitor is at least 5% less, at least 10% less, at least 25% less, at least 50% less, at least 60% less, at least 70% less, at least 80% less, or at least 90% less than the normal dosage (i.e. recommended dosage) of said NMDAR inhibitor when administered alone. According to some embodiments of the present disclosure, the therapeutically effective amount of the NMDAR inhibitor is 5-90% less, 10-90% less, 25-90% less, or 50-90% less than the normal dosage (i.e. recommended dosage) of said NMDAR inhibitor when administered alone.

In the method or pharmaceutical composition for treating depression of the present disclosure, the NMDAR inhibitor and the T-VSCC inhibitor can be formulated to be in a same composition, or alternatively, the NMDAR inhibitor is formulated in a first composition while the T-VSCC inhibitor is formulated in a second composition.

In the method or pharmaceutical composition for treating depression of the present disclosure, the NMDAR inhibitor and the T-VSCC inhibitor can be administered simultaneously, or alternatively, the NMDAR inhibitor and the T-VSCC inhibitor can be administered separately.

In the present disclosure, the term "depression" may specifically be referred to as lateral-habenula-mediated depression, and may, in more particular, be referred to as lateral-habenula-burst-mediated depression. The inventors of the present application have found and demonstrated that abnormal firing of neurons in the lateral habenula, especially the abnormal burst firing, plays an important role in the pathogenesis of depression. The inventors of the present application have also identified key factors affecting burst firing in the lateral habenula, and have further demonstrated that, by regulating one or more of these key factors, depression can be inhibited or even eliminated.

According to some embodiments of the present disclosure, in the method and the pharmaceutical agent for treating depression in a subject by inhibiting burst in lateral habenula or in the pharmaceutical composition for treating depression as provided herein, said method, pharmaceutical agent, or pharmaceutical composition is suitable for use in patients with depression to whom other anti-depression method and drugs are ineffective.

Herein, the other anti-depression drugs include, but are not limited to, the following types of drugs: melatonin (i.e. 5-hydroxytryptamine (5-HT)) agonists, selective serotonin reuptake inhibitors (SSRIs), serotonin and norepinephrine reuptake inhibitors (SNRIs), monoamine oxidase inhibitors (MAOIs), tricyclic antidepressants (TCAs), triple monoamine uptake blockers, metabotropic glutamate receptors (of mGluRs), GABA antagonist, NK1 antagonist, NK2 antagonist, CRF1 antagonist, arginine vasopressin V1b antagonists, MCH receptor antagonists, NT-3 antagonist, NT-4 antagonists, and CREB antagonist.

The above types of antidepressants and specific drugs are listed in international patent application publication number WO2007137247A2, which is hereby incorporated by reference in its entirety.

The inventors of the present application have for the first time found and demonstrated that the abnormal firings of neurons in the lateral habenula, especially the abnormal burst firing, plays an important role in the pathogenesis of depression. The inventors are able to provide method and medicaments for treating (i.e. inhibiting or suppressing) depression by inhibiting abnormal firings of neurons in lateral habenula, especially by inhibiting the abnormal burst firings. This is a pathological mechanism containing the target tissue in the brain and the molecular targets that currently known mechanisms and drugs have failed to target. Accordingly, the method, the pharmaceutical agent, and the pharmaceutical composition provided by the present disclosure are particularly suitable for the treatment of depression patients to whom the above-described anti-depression methods and drug are ineffective.

Certain NMDA receptor inhibitors are known in the field for the treatment of depression. However, in these reports, the anti-depression mechanisms that have been discovered or assumed are completely different than the anti-depression mechanism provided by the present disclosure, that is, by inhibiting the abnormal firings, and especially the abnormal burst firings, of neurons in the lateral habenula. Without affecting the novelty and inventive steps of the present disclosure, according to some embodiments, in the method and the pharmaceutical agent for treating depression in a subject by inhibiting burst in lateral habenula or in the pharmaceutical composition for treating depression as provided herein, said pharmaceutical agent for inhibiting burst does not include these NMDA receptor inhibitors listed above, such as AP5, CPPene, MK801, memantine, ketamine, felbamate, glycine, D-serine, D-cycloserine, or L-glutamic acid efendil, etc.

Certain compounds are known in the field to be able to inhibit T-type calcium channel, and they show certain anti-depression effects, such as Fluoxetine, trazodone, ethosuxamine, trimethyldione, sodium valproate, pimozide and zonisamide. However, in these reports, the anti-depression mechanism discovered or presumed are completely different than the anti-depression mechanism provided by the present disclosure, that is, by inhibiting the abnormal firings, and particularly the abnormal burst, of lateral habenula neurons. Without affecting the novelty and inventive steps of the present disclosure, according to some embodiments, in the method and the pharmaceutical agent for treating depression in a subject by inhibiting burst in lateral habenula or in the pharmaceutical composition for treating depression as provided herein, said pharmaceutical agent for inhibiting burst does not include fluoxetine, trazodone, ethosuxamine, trimethyldione, sodium valproate, pimozide or zonisamide.

According to some embodiments of the present disclosure, in the method and the pharmaceutical agent for treating depression in a subject by inhibiting burst in lateral habenula or in the pharmaceutical composition for treating depression as provided herein, said pharmaceutical agent capable of inhibiting burst firings does not inhibit firing of tonic pulse.

According to some embodiments of the present disclosure, in the method and the pharmaceutical agent for treating depression in a subject by inhibiting burst in lateral habenula or in the pharmaceutical composition for treating depression as provided herein, said method, pharmaceutical agent and pharmaceutical composition are configured to take effect locally in lateral habenula, that is, they are substantially method, pharmaceutical agent and pharmaceutical composition configured to be applied in lateral habenula. For methods and medicaments used on nervous tissues, particularly on those in the brain, such as the lateral habenula, it is beneficial to limit the effects of the drug or medicine to the target tissue. The administration of a medicine locally in the lateral habenula is a limiting technical feature to a method or a pharmaceutical agent for treating depression. In any method or pharmaceutical agent or medicament for LHb, whether the method or drug can take effects in LHb shall be considered, including whether the drug can reach LHb, and whether the effective concentration can be achieved in LHb, etc. According to some embodiments of the present disclosure, the medicament or pharmaceutical composition can be in a dosage form allowing for local administration to the lateral habenula. The action of the medicament can be limited to the target tissue by local administration, for example by formulating the medicament as a dosage form that can be administered locally to the lateral habenula by cannulation or by sleeve implantation. In another example, the drug can be formulated as a dosage form having sustained release after being implanted into the tissue. The above medicaments can also be formulated in the form of tissue-specific targeted drug delivery systems. For example, a small molecule compound or a biologically active molecule (e.g. nucleic acid such as a protein-encoding DNA or mRNA molecule, or a protein such as an antibody, etc.) capable of specifically binding to a protein expressed in the lateral habenula can be conjugated with an antibody or an antibody fragment that binds to cells of the lateral habenula to thereby form a complex molecule capable of recognizing and binding to lateral habenula.

According to some embodiments of the present disclosure, in the method (including administering a NMDAR inhibitor only, administering a T-VSCC inhibitor only, or administering a combination of a NMDAR inhibitor and a T-VSCC inhibitor) and the pharmaceutical agent (including the pharmaceutical composition or a combination pharmaceutical compositions) for treating depression by inhibiting burst in the lateral habenula, said T-VSCC inhibitor can include Fluoxetine, trazodone, ethosuxamine, trimethyldione, sodium valproate, pimozide or zonisamide; and said NMDA receptor inhibitors can be AP5, CPPene, MK801, memantine, ketamine, felbamate, glycine, D-serine, D-cycloserine, L-glutamic acid efendil, and the like.

According to some embodiments of the present disclosure, the method and the pharmaceutical agent, and the pharmaceutical composition for treating depression by inhibiting burst in the lateral habenula, are configured to allow for fast treatment of depression.

Herein, the "fast treatment", "fast-acting", or "rapidly", or alike, is defined as a treatment that can take an effect within a range of around half an hour to four hours. It is noteworthy that most existing antidepressants in the field generally take a week to several weeks to exert antidepressant effects. For example, the commonly used 5-HT reuptake inhibitors (SSRI) are usually effective in 2-3 weeks; 5-HT and serotonin and norepinephrine reuptake inhibitors are usually only effective after 1 week. The anti-depression methods and the medicaments or pharmaceutical compositions provided by the present disclosure can have an onset time of less than one week, preferably less than three days, more preferably less than one day, such as less than 12 hours. Some embodiments of the medicament provided by the present disclosure allow for fast-acting treatment of depression with an intermediate-term or long-term effect, wherein a single-dose anti-depression effect can last for more than one day, preferably for more than three days, more preferably for more than one week.

According to some embodiments, the present disclosure provides a pharmaceutical composition comprising a therapeutically effective amount of a pharmaceutical agent capable of inhibiting burst in lateral habenula.

Herein, the active ingredient, component, or substance in the pharmaceutical composition provided by the present disclosure can be a pharmaceutical agent that is capable of inhibiting burst in lateral habenula.

According to some embodiments, the active ingredient in the pharmaceutical composition is in the form of a raw compound. Optionally, the active ingredient in the pharmaceutical composition can also be in the form of a physiologically or pharmaceutically acceptable salt. Further optionally, the pharmaceutical composition can further comprise one or more adjuvants, excipients, carriers, buffers, diluents, and/or other pharmaceutically acceptable auxiliary substances that is or are pharmaceutically compatible with the active ingredient or the pharmaceutically acceptable salt thereof.

The pharmaceutical composition provided herein may be administered through any convenient route, which suits a therapy need. Optionally, the routes of administration can include oral administration, and as such, the pharmaceutical composition can be in a solid form including tablets, capsules, pastilles, powders, or in a liquid form. Further optionally, the routes of administration can include parenteral administration, such as cutaneous, subcutaneous, intramuscular, or intravenous injection. The pharmaceutical composition of the disclosure can be manufactured by people of ordinary skills in the field by use of standard methods and conventional techniques that are appropriate to the desired formulation. When desired, compositions adapted to giving sustained release of the active ingredient may be employed.

The pharmaceutical composition provided herein may be optionally configured for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or may be optionally configured for administration by inhalation or insufflation, including powders and liquid aerosol administration, or may be optionally configured for sustained release. Examples of sustained release system can include semipermeable matrices of solid hydrophobic polymers containing the compound of the disclosure, where the matrices may be in form of shaped articles, e.g. films or microcapsules.

The active ingredient in the pharmaceutical compositions, together with a conventional adjuvant, carrier, or diluent, may thus be placed into the form of pharmaceutical compositions and unit dosages thereof. Such forms include solid forms, and in particular tablet forms, filled capsule forms, powder forms, and pellet forms, and may further include liquid forms, in particular aqueous or non-aqueous solutions, suspensions, emulsions, elixirs, and capsules filled with the same, for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the active ingredient of the present disclosure, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring reagents, solubilizers, lubricants, suspending reagents, binders, preservatives, tablet disintegrating reagents, or an encapsulating material.

Aqueous solutions suitable for oral use can be prepared by dissolving the active component in water and adding suitable colorants, flavours, stabilising and thickening reagents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending reagents.

Also included are solid form preparations, which are intended for conversion shortly before use to liquid form preparations for oral administration. Such liquid forms include solutions, suspensions, and emulsions. In addition to the active component such preparations may comprise colorants, flavors, stabilizers, buffers, artificial and natural sweeteners, dispersants, thickeners, solubilizing reagents, and the like.

For topical administration to the epidermis the chemical compound of the disclosure may be formulated as ointments, creams or lotions, or as a transdermal patch. Ointments and creams may, for example, be formulated with an aqueous or oily base with the addition of suitable thickening and/or gelling reagents. Lotions may be formulated with an aqueous or oily base and will in general also contain one or more emulsifying reagents, stabilizing reagents, dispersing reagents, suspending reagents, thickening reagents, or coloring reagents.

Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

Where desired, compositions adapted to provide a sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be in a packaged form containing an appropriate number of unit dosage forms.

Throughout the disclosure, the terms "therapeutically effective amount", "therapeutically effective dose", or alike, are referred to as an amount of active ingredient that is capable of ameliorating symptoms or condition at issue. Therapeutic efficacy and toxicity, e.g. ED50 and LD50, may be determined by standard pharmacological procedures in cell cultures or experimental animals. The dose ratio between therapeutic and toxic effects is the therapeutic index and may be expressed by the ratio LD50/ED50.

The dose administered can be carefully adjusted to the age, weight and condition of the individual being treated, as well as the route of administration, dosage form and regimen, and the result desired, and the exact dosage should be determined by the practitioner.

The actual dosage depends on the nature and severity of the disease being treated, the exact mode of administration and form of administration, and is within the discretion of the physician, and may be varied by titration of the dosage to the particular circumstances of this disclosure to produce the desired therapeutic effect. However, it is presently contemplated that the pharmaceutical composition containing of from about 0.1 to about 1000 mg of active ingredient per individual dose, preferably of from about 1 to about 750 mg are suitable for therapeutic treatments.

The present disclosure also provides an animal model of depression, which can be a rat or a mouse. The animal model of depression provided herein shows symptoms of depression, and has abnormal burst firings in lateral habenula.

The present disclosure also provides a method for screening potential substances for treating depression using the above mentioned animal model, comprising the steps of:

(1) administering a test substance to be screened to an animal model of depression; and (2) observing the symptoms and/or indicators associated with depression in the animal model of depression and comparing it with the control group.

If the symptoms associated with depression in the animal model of depression are significantly improved, it indicates that the test substance is a substance that can potentially be used to treat depression.

According to some embodiments of the disclosure, the method of screening for a potential substance for treating depression further comprises one or more of the following steps:

the potential substances screened in the previous step are further tested for their effects on burst firing in neurons; and the potential substances screened in the previous step are administered to animal models to observe their effects on symptoms of depression.

When testing the effect on the burst firing in neurons, if the ratio of burst in neurons in the test group to which the test substance was added or administered is significantly lower than that of the negative control group (or the blank control group), it means that the test substances are potential substances for the treatment of depression.

BRIEF DESCRIPTION OF THE DRAWINGS

FIGS. 1A-1I show local blockade of NMDARs in LHb is sufficient to elicit rapid and sustained antidepressant effects. FIG. 1A, Illustration of bilateral implantation of cannulae in LHb of cLH rats. CTX: cortex; HPC: hippocampus. Bottom: white dashed lines indicate location of habenula. FIGS. 1B-1G, Acute antidepressant effects of local bilateral infusion of ketamine (25 μg, 1 ul each side, 1 h, B-D), AP5 (40 nmol, 1 ul each side, 0.5 h, E-G) in LHb in forced swim test (FST, C, F) and sucrose preference test (SPT, D, G). Infusion sites of drugs are verified by CTB (B, E, see Methods). FIGS. 1H-1I, Sustained antidepressant effects of local bilateral infusion of ketamine (25 ug, 1 ul each side, 14 d) in LHb in forced swim test (FST, H) and sucrose preference test (SPT, I). Data are mean±s.e.m. P<0.01, *P<0.005, n.s. not significant.

FIGS. 2A-2N show bursting activity is enhanced in rat and mouse model of depression, which is reversed by ketamine. FIG. 2A, Whole cell patch recordings sites across different subregions of LHb. FIGS. 2I-2N, Bursting neurons are significantly increased in cLH rat model (FIGS. 2I-2K) and chronic restraint stress (CRS) mouse model (FIGS. 2L-2N) of depression, which is reversed by ketamine. FIGS. 2I and 2L, Pie charts illustrating the percentage abundance of the three types of LHb neurons in SD and cLH rats (FIG. 2I), or control and CRS mice (FIG. 2L). FIGS. 2J and 2M, Bar graph illustrating the percentage of burst- and tonic-type spikes in all spikes recorded. FIGS. 2K and 2N, Histogram of inter-spike intervals (ISI, ms) distribution. Data are mean±s.e.m. *P<0.05, P<0.01, **P<0.0001.

FIG. 3A, Recording sites of each tetrode track in LHb of CRS and control mice. FIG. 3B, Example traces (left) and averaged spike waveform (right) of recorded neurons from LHb of control (top), CRS (middle) and the same CRS unit after ketamine injection (bottom). Bursts (red shades) are identified by ISI method (see Methods). FIGS. 3C-3D, Percent of spikes in bursting mode and number of bursts per minute of neurons recorded from control, CRS mice (FIG. 3C), and the same unit in CRS mice 1 h before and after ketamine injection (FIG. 3D). FIG. 3E, Cumulative distribution of ISI from control, CRS mice, and CRS mice treated with ketamine. Dashed lines indicate the 50% percentile of ISI (control: 143 ms; CRS: 33 ms, CRS+ketamine: 121 ms). FIG. 3F, Spike-triggered averages (STAs) of neurons recorded from control, CRS, and CRS mice after ketamine injection. Note the distance between the neighboring troughs is around 140 ms (corresponding to 7 Hz) in CRS mice. FIG. 3G, Spike-field coherence (SFC) of neurons recorded from control, CRS, and CRS mice after ketamine injection. Left: SFC of each unit; Middle: average SFC; Right: percent SFC in theta band (4-10 Hz). Data are mean±s.e.m. *P<0.05, *P<0.001, **P<0.0001.

FIGS. 4A-4J show LHb bursting requires activation of NMDARs. FIG. 4A, Example traces showing evoked EPSCs when the cells are held at −80 mV. NMDAR-EPSCs are isolated by application of picrotoxin and NBQX in $Mg^{2+}$ free ACSF, and confirmed by AP5 blockade. FIG. 4B, Amplitudes of NMDAR-EPSCs under different voltages (EPSCs are recorded under 0 $Mg^{2+}$, picrotoxin and NBQX); the isolated NMDAR-EPSCs is completely blocked by AP5. FIGS. 4C-4H, Example traces (left) and statistics (right, sampled within 1 min after drug application) showing effects of ketamine (FIGS. 4C-4D), AP5 (FIGS. 4E-4F) or NBQX (FIGS. 4G-4H) on spontaneous bursts in LHb. Spikes in bursting mode are marked in blue. Spikes in tonic-firing mode are marked in black. FIG. 4I, Example trace of an originally silent LHb neurons induced to bursts by NMDA perfusion and returned to silence after ketamine application. Note that NMDA induces both large EPSP (green shaded) and bursting discharges. FIG. 4J, Summary of NMDA perfusion and ketamine effect on bursting. Data are mean±s.e.m., *P<0.05, P<0.01, *P<0.001.

FIGS. 5A-5J show LHb bursting requires membrane hyperpolarization and T-VSCCs. FIG. 5A, Representative trace of a LHb neuron transformed from bursting- to tonic-firing mode with a ramp-like current injection, showing bursting at more hyperpolarized potential and tonic firing at more depolarized membrane potential. Spikes in bursting and tonic-firing mode are marked in blue and black respectively. FIG. 5B, Percentage of LHb neurons that can be induced into bursting mode with a hyperpolarizing current injection during the current ramp. Number in the bar indicates cell number. FIGS. 5C-5E, Correlations of membrane potential versus inner burst frequency (FIG. 5C), burst duration (FIG. 5D) and inner burst spike number (FIG. 5E) generated by current ramps. FIGS. 5F and 5G, Example trace (left) and statistics (right) of a spontaneously tonic-firing neuron transformed to burst-firing mode by hyperpolarization (FIG. 5F), and a spontaneously bursting neuron transformed to tonic firing by depolarization (FIG. 5G). FIGS. 5H-5I, Example traces (left) and statistics (right, sampled within 1 min after drug application) showing effects of T-VSCC blocker miberfradil (FIG. 5H) or HCN blocker ZD7288 (FIG. 5I) on spontaneous bursts in LHb. FIG. 5J, An example trace summarizing the ionic components and channel mechanisms involved in LHb bursting. Activation of T-VSCCs removes the Mg blockade of NMDARs. The opening of these two channels synergistically drive membrane potential toward the threshold for a burst of APs. After the quick inactivation of T-VSCCs and NMDARs, the return of RMP back to below −55 mV de-inactivates T-VSCCs, which initiates another cycle of burst. Data are mean±s.e.m., *P<0.05, **P<0.01, n.s. not significant.

FIGS. 6A-6C show local bilateral infusion of mibefradil in LHb exerts a rapid antidepressant effect in FST (FIG. 6B) and SPT (FIG. 6C). Infusion sites are verified by CTB (FIG. 6A). Data are mean±s.e.m., *P<0.005, **P<0.01, n.s. not significant.

FIGS. 7A-7H show eNpHR-induced rebound burst drives behavioral aversion and depressive-like symptoms. FIG. 7A, Construct of AAV2/9-eNpHR3.0 (top), example site of viral injection and optic fiber implantation (middle), and illustration of optrode recording (bottom). FIGS. 7B-7C, Representative traces showing rebound bursts reliably elicited by pulsed yellow light in LHb brain slices in vitro (FIG. 7B) and in vivo from mice infected with AAV2/9-eNpHR3.0. Spikes in bursting and tonic-firing mode are marked in blue and black respectively. Percentage of successfully induced burst is shown on right. FIG. 7D, Raster plots (top) and post-stimulus time histogram (bottom) of an example LHb neuron responding to 100 ms yellow light stimulation from in vivo optrode recording. FIG. 7E, Distribution of intra burst frequencies and intra burst spike numbers of eNpHR3.0-driven rebound bursts (left) are comparable to those in CRS mice (right). Means are represented by the black crosses. FIG. 7F, Real-time place aversion (RTPA) induced by eNpHR3.0-driven bursts. Left: representative heat maps of RTPA; Right: quantitative aversion score (see Methods). FIGS. 7G-7H, Depressive-like behaviors in FST (FIG. 7G) and SPT (FIG. 7H) induced by eNpHR3.0-driven bursts. Data are represented as mean±s.e.m., **P<0.01.

FIG. 8A, Representative trace showing LHb neurons following a 5 Hz tonic blue light stimulation protocol in LHb brain slices infected with AAV2/9-oCHIEF. Percentage of responsive neurons shown on the right. FIGS. 8B-8C, 5 Hz photostimulation of mice expressing oChIEF does not change locomotion in OPT (FIG. 8B), and does not induce depressive phenotypes in FST (FIG. 8C).

FIGS. 10A-10B, Example traces (left) and statistics (right) showing effects of ketamine (FIG. 10A) or AP5 (FIG. 10B) on rebound burst. Current injection steps are illustrated under the bottom of the trace. FIG. 10C, Example traces (left) and statistics (right) showing effects of T-VSCC blocker miberfradil on rebound bursts. FIGS. 10D-10E, Example traces (left) and statistics (right) showing effects of combined application of mibefradil and AP5 (FIG. 10D) or mibrfradil and ketamine (FIG. 10E) on rebound bursts. Data are mean±s.e.m., ****P<0.0001.

DETAILED DESCRIPTION

Figure 1F:
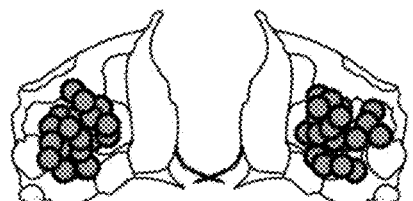
Figure 1F:
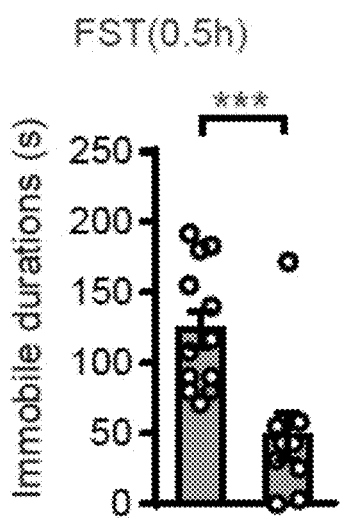

The technical details and benefits of the invention provided in the present disclosure are further described in the following examples, which are intended to illustrate the inventions and not to limit the scope of the present disclosure.

Example 1. Materials and Methods

Animals. Male cLH rats (8-16 weeks of age) and age-matched male Sprague Dawley rats (SLAC Laboratory Animal Co., Shanghai) were used. The cLH rats were screened by learned helpless test for breeding as previously described (Schulz et al., 2010). Male adult (8-16 weeks of age) C57BL/6 mice (SLAC) were used for establishing the chronic restraint stress (CRS) depression model. Rats were group-housed two/cage and mice were four/cage respectively under a 12-h light-dark cycle (light on from 7 a.m. to 7 p.m.) with free access to food and water ad libitum. All animal studies and experimental procedures were approved by the Animal Care and Use Committee of the animal facility at Zhejiang University.

Viral vectors. AAV2/9-CaMKII-eNpHR3.0-eYFP (titer: $7.45 \times 10^{12}$ v.g./ml, dilution: 1:5, 0.1 µl unilateral into LHb, Taitool Bioscience, China), AAV2/9-Ubi-eGFP (titer: $2.5 \times 10^{13}$ v.g./ml, 1:30, 0.1 µl each side of LHb, University of Massachusetts, Guangping Gao Lab, USA), AAV2/9-hSyn-oChIEF-tdTomato (titer: $6.29 \times 10^{12}$ v.g./ml, 1:5, 0.1 µl unilateral into LHb, Obio Technology, Shanghai, Corp., Ltd) were aliquoted and stored at −80° C. until use.

Cannula infusion experiment. A 26-gauge double guide cannulae (center-to-center distance 1.4 mm, Plastics One) was placed with a 2-degree angle with coronal plane (without the 2 degree rotation, we found it difficult to hit both sides of LHb) and inserted bilaterally into the LHb (AP, −3.7 mm from bregma; ML, ±0.7 mm; DV, −4.1 mm from the brain surface) of cLH rats. A 33-gauge double dummy cannulae (Plastic One), secured with a dust cap, was inserted into guide cannula to prevent clogging during recover period. After rats were recovered for at least 7 days, drugs were microinjected with a 33-gauge double injector cannulae, which has a 0.6 mm extension beyond the tip of the guide cannula, while cLH rats were anaesthetized with isoflurane on an anesthetic machine. The extensions were manually sharpened before insertion.

Ketamine (25 µg/µl), AP5 (40 nmol/µl, IC50=30 µM), NBQX (1 nmol/µl, IC50=0.15 µM) or mibefradil (10 nmol/µl) were dissolved in 0.9% saline respectively. Ketamine was purchased from Gutian Pharma Co., Fujian, and stored at room temperature. Before the drug local infusion, tip-sharpened 33-gauge double injector cannulae were inserted into the guide cannulae to assure clear passage and then pulled out. 1 µl of drug was infused (0.1 µl/min) into each side through another tip-sharpened 33-gauge double injector cannulae, which were connected to the microsyringe. The injector cannulae were left in place for an additional 10 min to minimize spread of the drug along the injection track. FST or SPT was performed 1 h after the injection of ketamine or mibefradil, 0.5 h after the injection of AP5 or NBQX. To verify the drug infusion sites, rats were injected with 1 μl CTB-488 to each side of LHb after all behavioral tests. For immunostaining, rats were then euthanized 30 min after CTB injection and processed as described. Brain slices were counterstained with Hoechst before mounting on the slides. Fluorescent image acquisition was performed with an Olympus VS120® virtual microscopy slide scanning system. Only data from rats with correct injections were used.

LHb brain slice preparation. Animals (P45-70 rats and P65-75 mice) were anesthetized with isoflurane and 10% chloral hydrate, and then perfused with 20 ml ice-cold ACSF (oxygenated with 95% $O_2$+5% $CO_2$) containing (mM): 125 NaCl, 2.5 KCl, 25 $NaHCO_3$, 1.25 $NaH2PO4$, 1 $MgCl_2$ and 25 Glucose, with 1 mM pyruvate added. The brain was removed as quickly as possible after decapitation and put into chilled and oxygenated ACSF. Coronal (for most of experiments if not specified) or sagittal slices containing habenular (350 μm- and 300 μm-thickness for rats and mice, respectively) were sectioned in cold ACSF by a Leica2000 vibratome and then transferred to ASCF at 32° C. for incubation and recovery. ACSF was continuously gassed with 95% $O_2$ and 5% $CO_2$. Slices were allowed to recover for at least 1 hour before recording. For cLH rats, since a very high percentage (90%) of cLH offsprings are learned helpless, we did not perform LH test before taking them for brain slice recording. For CRS mice, both CRS and their wild-type controls went through FST test before brain slice recording. We then used the CRS animals which showed high immobility scores (immobile time >140 s) and control mice which showed low immobility (immobile time <110 s) in FST for slice recording.

In vitro Electrophysiological recording. For LHb neuron recordings, currents were measured under whole-cell patch clamp using pipettes with a typical resistance of 5-6 MΩ filled with internal solution containing (mM): $10^5$ K-Gluconate, 30 KCl, 4 Mg-ATP, 0.3 Na-GTP, 0.3 EGTA, 10 HEPES and 10 Na-phosphocreatine, with pH set to 7.35. The external ACSF solution contained (in mM) 125 NaCl, 2.5 KCl, 25 $NaHCO_3$, 1.25 $NaH_2PO_4$, 1 $MgCl_2$, 2 $CaCl_2$ and 25 Glucose. Cells were visualized with infrared optics on an upright microscope (BX51WI, Olympus). A MultiClamp 700B amplifier and pCLAMP10 software were used for electrophysiology (Axon Instruments). The series resistance and capacitance was compensated automatically after stable Giga seal were formed. Recordings were typically performed between 3-6 min after break-in. The spontaneous neuronal activity was recorded under current-clamp (I=0 pA).

LHb neurons display three modes of spontaneous activity at resting conditions. Silent cells showed no spike activities during recording. Tonic cells spontaneous generated tonic trains of action potentials at frequency between 0.1-10 Hz, rarely up to 10-20 Hz. Burst-firing cells spontaneously generate clusters of spikes with an initially high but progressively declining intra-burst firing frequency in each burst. For bursting neurons, 99% (from n=50 bursting neurons) of their spikes occurred within bursts.

Evoked-NMDAR-EPSC was recorded under voltage clamp from −50 mV to −80 mV in a modified extracellular ACSF solution with 0 $Mg^{2+}$. Evoked T-type VSCC current was recorded under voltage clamp starting from a holding potential of −50 mV before increased to conditioning potential (−100 mV) for is preceding the command steps (5 mV, 0.1 Hz/step increment). LHb T-VSCC currents were obtained by subtraction of recorded traces in presence or absence of mibefradil.

In vivo electrophysiology. For in vivo recording experiments, a custom-made microdrive array consisting of 8 tetrodes (impedance 250-500 KΩ, California fine wire) was implanted in LHb (AP, −1.72 mm; ML, 0.46 mm; DV, −2.44 mm from the brain surface) of Ctrl or CRS mice. Stainless steel wires were attached to two screws on the skull as ground. The microdrive was secured to the skull with dental cement. After recovery for 2 weeks, mice were allowed to adapt to the recording headstage 10 min per day for 2-3 days. Spontaneous spiking activity (digitized at 40 kHz, band-pass filtered between 300-6000 Hz) and LFP (digitized at 1 kHz sampling rate, low-pass filtered up to 250 Hz) were recorded simultaneously for 30 min during the still period of the mice in their home cages with a gain of 5000×. A single channel without detectable unit was assigned as a reference electrode. The tetrodes were lowered insteps of 70 μm after each recording session followed with at least 2 day-recovery. For CRS mice, data were recorded for 30 min before and 1 h after ketamine treatment (10 mg/kg, i.p.). If mice received a second ketamine injection, at least a 2-week interval was introduced before the next recording session. All procedures were performed during the light phase. The positions of the electrodes were verified by electrolytic lesions (30 μA, 10-15 s) at the end of all the experiments.

Spike sorting. All waveforms recorded from each tetrode were imported in Offline Sorter V3 (Plexon Inc.). Single units were manually identified by threshold crossing and principal component analysis (PCA). Spikes with inter-spike interval (ISI) less than the refractory period (1.4 ms) were excluded. Cross correlograms were plotted to ensure that no cell was discriminated more than once on overlapping tetrodes. Only units with signal to noise ratio larger than 2 were used.

Behavioral assays. All behavioral assays were performed on animals 12-16 weeks old, in the light cycle (7:00-19:00) except for the sucrose preference test, which was performed during dark phase to maximize the consumption of solutions. Behavioral analysis was performed blindly.

Forced swim test (FST). Animals were individually placed in a cylinder (12 cm diameter, 25 cm height for mice; 20 cm diameter, 50 cm height for rats) of water (23-24° C.) and swam for 6 min under normal light. Animal behaviors were videotaped from the side. The immobile time during the last 4 min test was counted offline by an observer blind of the animal treatments. Immobile time was defined as time when animals remained floating or motionless with only movements necessary for keeping balance in the water. For rats, an additional pre-test was conducted 24 h before the test, during which rats were individually placed in a cylinder of water with conditions described above for 15 min. For optogenetic manipulations, laser stimulation was turned on as previously described, immediately after mice were placed in the water and lasted for 6 min. In order to minimize the impact of the optogenetic cable on swimming behavior, the cable length was adjusted to allow the cable just touch the water surface.

Sucrose preference test (SPT). Animals were single housed and habituated with two bottles of water for 2 days, followed by two bottles of 2% sucrose for 2 days. Animals were then water deprived for 24 h and then exposed to one bottle of 2% sucrose and one bottle of water for 2 h in the dark phase. Bottle positions were switched after 1 h. Total consumption of each fluid was measured and sucrose preference was defined as the ratio of sucrose consumption divided by total consumptions of water and sucrose. For optogenetic manipulations, mice were gently placed in a white arena containing normal bedding and allowed to freely move in the arena. During the 90-min test, light was delivered during 30-60 min. Laser intensity during eNpHR3.0 stimulation was adjusted to 10 mW since LHb neurons could not follow 16 mW stimulation for longer than 10 min. Sucrose preference scores were measured for every 30 min. Only animals that had a >30% baseline sucrose preference during the first 30 min session would proceed to the next session. Otherwise they would be tested later on a different day. Behavioral analyses and experiments were performed blindly.

Chronic restraint stress (CRS). Mice were subjected to chronic-restraint stress by placement in 50-ml conical tubes with holes for air flow for 2-3 hours per day for 14 consecutive days. ROC curve (Receiver Operating Characteristic curve) of immobile time in forced-swim test was used to assess the successful rate of CRS on depressive-like behaviors. The nearest point to (0, 100) on ROC curve was selected as successful rate according to GraphPad Statistics Guide.

Real-time place aversion. Mice were placed in a white open chamber (52 cm×26 cm×23 cm) consisting of two chambers, and allowed to freely move between chambers for 20 minutes to assess their baseline place preference. During the following 20-min test, we assigned a stimulated side with a counterbalanced manner. Laser stimulation was turned on as previously described, as soon as mice entered the stimulated side and terminated once mice crossed to the non-stimulated side. A video camera positioned above the chamber recorded each trial. Mouse locations and velocity were tracked and analyzed using Any-maze Software (Stoelting Co.). Avoidance score=(Time in stimulated side−Time in non-stimulated side)$_{test}$−(Time in stimulated side−Time in non-stimulated side)$_{baseline}$ Open field test (OFT). Animals were placed in the center of an arena (40 cm×40 cm×40.5 cm for mice; and 100 cm×100 cm×50 cm for rats) in a room with dim light for 6 min. A video camera positioned directly above the arena was used to track the movement of each animal (Any-maze, Stoelting, US). For optogenetic manipulations, mice were allowed to freely move throughout the arena for 9 min, with laser stimulation occurring during the middle 3 min epoch (eNpHR3.0: 589 nm, 1 Hz, 16 mW, 100 ms pulses; oChIEF: 473 nm, 100 Hz, 25 mW, either 5 ms pulses, 5 pulses/s for the pulsed 100 Hz protocol or 5 Hz, 5 ms pulses for the 5 Hz protocol).

Statistical analysis. Required sample sizes were estimated based on our past experience performing similar experiments. Mice were randomly assigned to treatment groups. Analysis were performed in a manner blinded to treatment assignments in all behavioral experiments. Statistical analyses were performed using GraphPad Prism software v6. By pre-established criteria, values were excluded from the analyses if the viral injection or drug delivering sites were out of LHb. All statistical tests were two-tailed, and significance was assigned at $P<0.05$. Normality and equal variances between group samples were assessed using the D'Agostino & Pearson omnibus normality test and Brown-Forsythe tests respectively. When normality and equal variance between sample groups was achieved, one-way ANOVAs (followed by Bonferroni's multiple comparisons test), or t test were used. Where normality or equal variance of samples failed, Kruskal-Wallis one-way ANOVAs (followed by Dunn's correction), Mann-Whitney U test, or Wilcoxon matched-pairs signed rank test were performed. Linear regression test, Chi-square test, Fisher's exact test or two-way ANOVAs (followed by Bonferroni's multiple comparisons test) was used in appropriate situations.

Figure 1G:
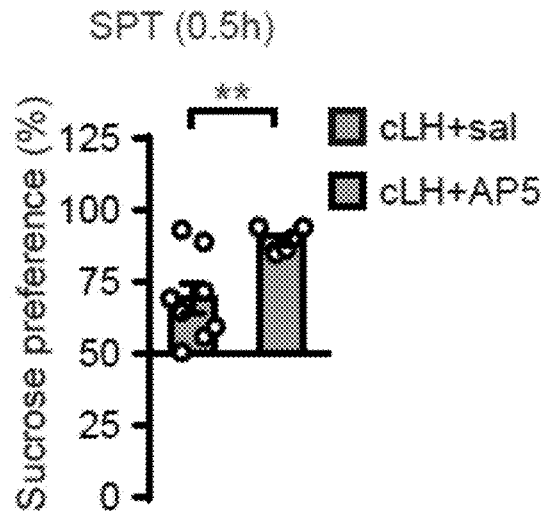
Figure 1H:
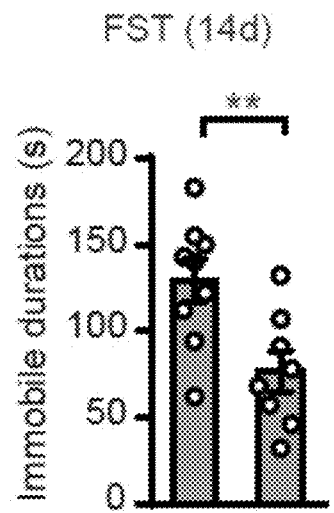
Figure 1I:
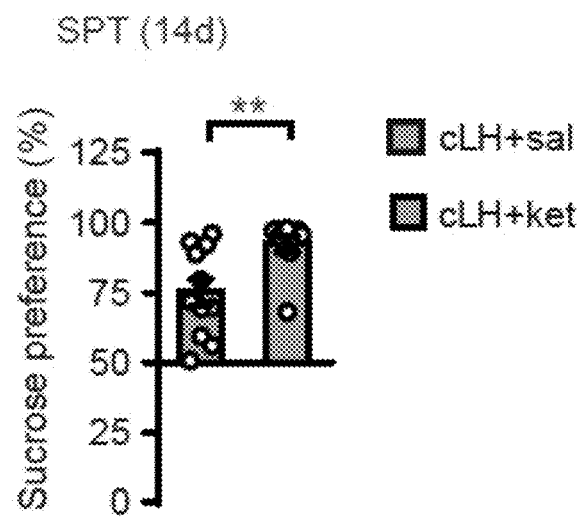

Example 2. Local Blockade of NMDARs in LHb is Sufficient to be Rapid Antidepressant The antidepressant effect of ketamine was tested on a well-accepted animal model of depression, the congenitally learned helpless (cLH) rats. It was tested whether ketamine may exert its antidepressant effect through LHb by performing bilateral infusion of ketamine in the LHb through dual guide cannulae (FIG. 1A). Local infusion of ketamine (25 ug, 1 ul each side) in the LHb of cLH rats was sufficient to quickly rescue the depressive-like behaviors, including the behavioral despair as measured by the immobility time in the FST (FIG. 1C) and the anhedonia as measured by the sucrose preference test (SPT FIG. 1D) 1 hr after infusion. To determine whether NMDAR inhibition is the main mechanism underlying the antidepressant effects of ketamine, a specific NMDAR antagonist AP5 (40 nmol, 1 ul, each side) was locally infused in the LHb, and found that AP5 efficiently reduced the immobile time in the FST (FIG. 1F), as well as increased hedonic behaviors in the SPT (FIG. 1G), similarly as ketamine. Indeed, infusion of ketamine (25 ug, 1 ul each side) into LHb of cLH rats induced sustained antidepressant effects for 14 days after injection (FIGS. 1H and 1I). All these results suggest that LHb local infusion of NMDAR antagonist can induce rapid and sustained antidepressant effect.

Figure 2A:
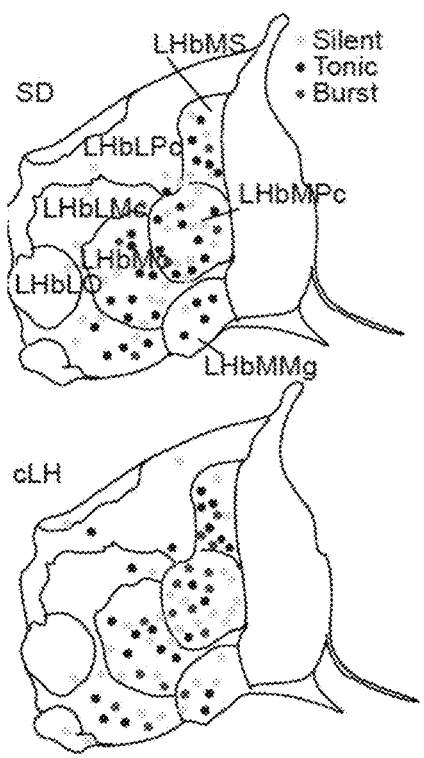
Figure 2B:
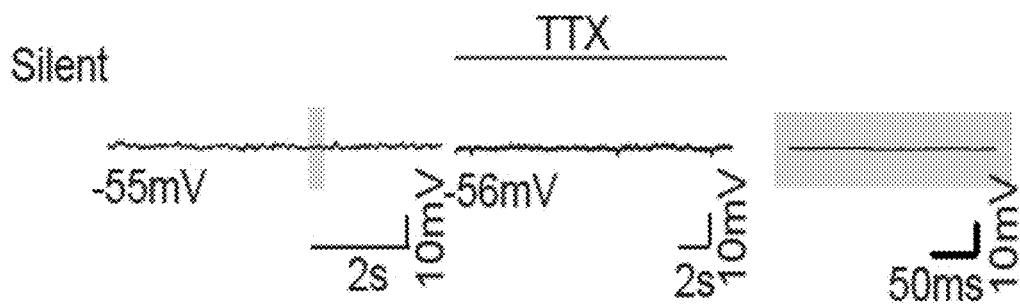
FIGS. 2B-2D, Representative traces showing spontaneous activity of three LHb neuron types, namely silent (FIG. 2B), tonic (FIG. 2C), and burst (FIG. 2D) firing types. Grey shaded areas shown at the right with enlarged time scales to illustrate shape of spike pattern. Red traces are responses of same neurons after TTX treatment.
Figure 2C:
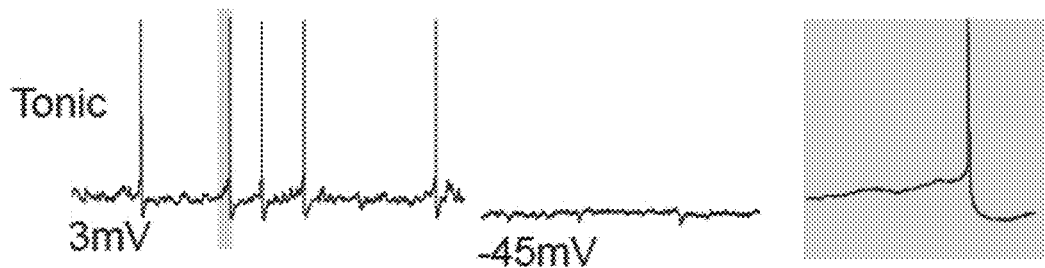
Figure 2D:
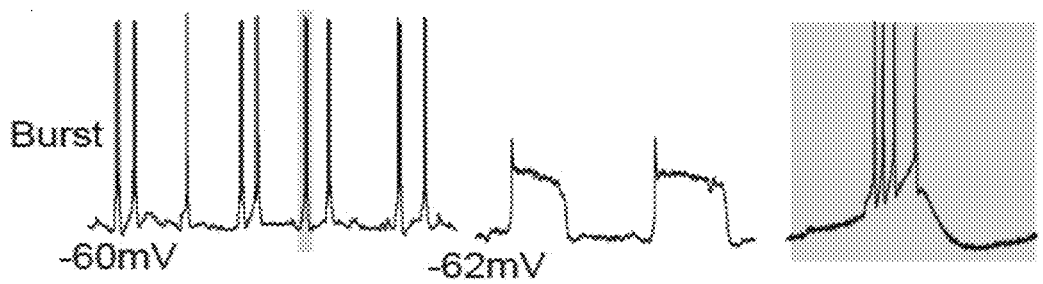

Example 3. Three Types of LHb Neurons, the Silent, Tonic and Burst Firing Types To investigate the activity pattern of the LHb neurons, whole cell patch clamp is performed in the LHb coronal slices, and recorded spontaneous neuronal activity under current clamp at resting conditions (I=0 pA). It was found that LHb neurons were intrinsically active and fell into three categories, namely, the silent, tonic- and burst-firing types (FIGS. 2A-2D). The three classes of neurons were distributed among different sub-nuclei of the LHb with no clear subregion enrichment (FIG. 2A).

Figure 2E:
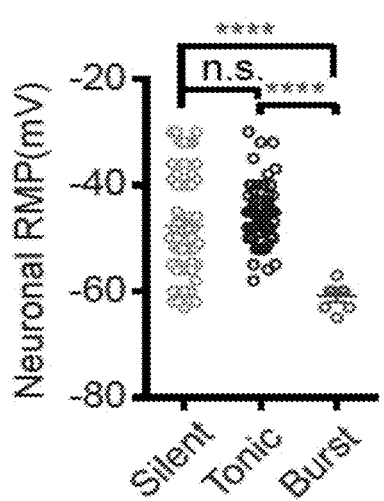
FIGS. 2E-2F, Scattered plots (FIG. 2E) and cumulative curves (FIG. 2F) denoting the mean and distribution of resting membrane potentials (RMPs).
Figure 2F:
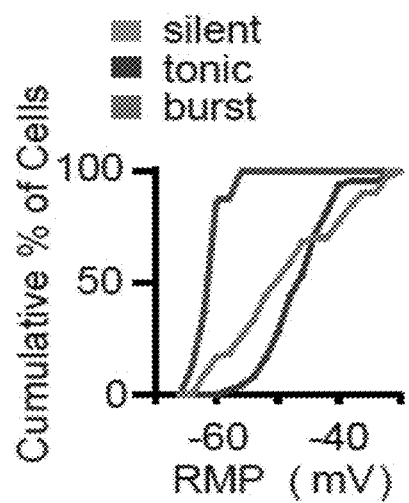

The resting membrane potentials (RMPs) of LHb neurons were on average more depolarized than those in the hippocampus or cortex (FIGS. 2E and 2F). Notably, the bursting neurons have significantly more hyperpolarized RMPs compared with the silent and tonic firing neurons (Silent: −47.8±1.3 mV, tonic: −45.5±0.8 mV, bursting: −61±0.9 mV, FIGS. 2E and 2F).

Figure 2G:
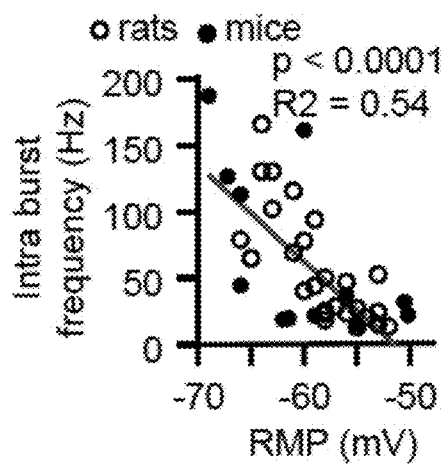
FIGS. 2G-2H, Intra burst frequency (FIG. 2G) but not inter burst frequency (FIG. 2H) reversely correlated with RMPs.
Figure 2H:
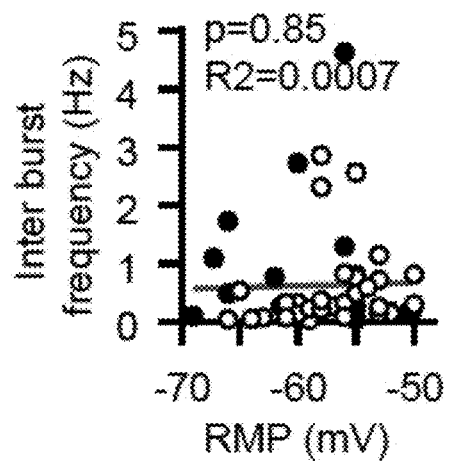
Figure 2I:
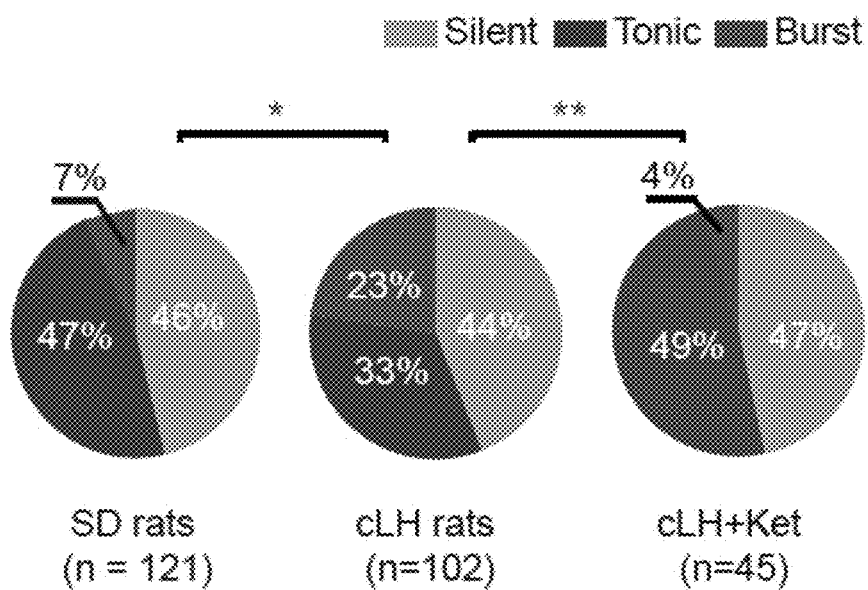
Figures 2J, 2K:
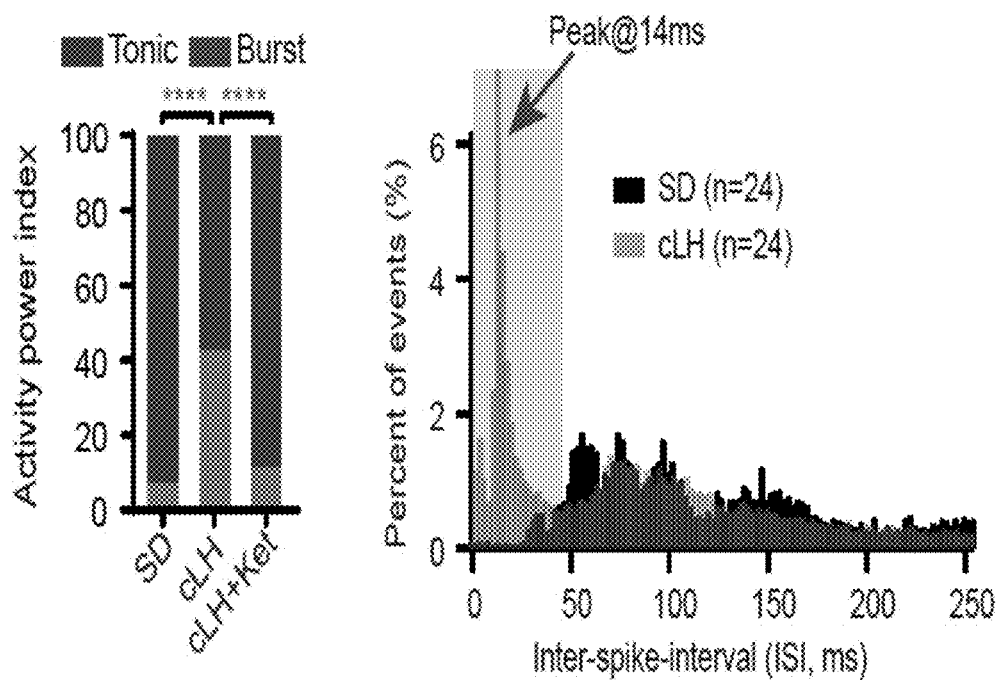

To test the potential contribution of bursting activity in the hyperactive state of the LHb under depression, the spike patterns of LHb neurons from the cLH or wild type SD rats were compared. While the percentage of bursting neurons was significantly increased from 7% (n=8/121) in the SD controls to 23% (n=21/102) in the cLH rats (FIG. 2I). The percentage of spikes in the bursting mode was also increased from 7% in SD to 43% in the cLH rats (FIG. 2J). It was then analyzed the inter-spike intervals (ISI), which represent the duration of the silent periods between two neighboring single spikes. A typical bursting cell shows a bimodal distribution of ISIs since it is composed of relatively large inter-burst intervals and small intra-burst intervals. In contrast, tonic firing cells show a more homogenous Poisson's distribution of ISIs. The ISIs of LHb neurons in SD rats were mostly normally distributed between 50 to 150 ms (n=24 neurons, FIG. 2K). In contrast, ISIs of LHb neurons from cLH rats exhibited a clear bimodal distribution with an extra sharp and condensed cluster of high frequency events centered around 14 ms (corresponding to ~71 Hz), indicating a significant weight increase of burst firings (n=24 neurons, FIG. 2K).

Figure 2L:
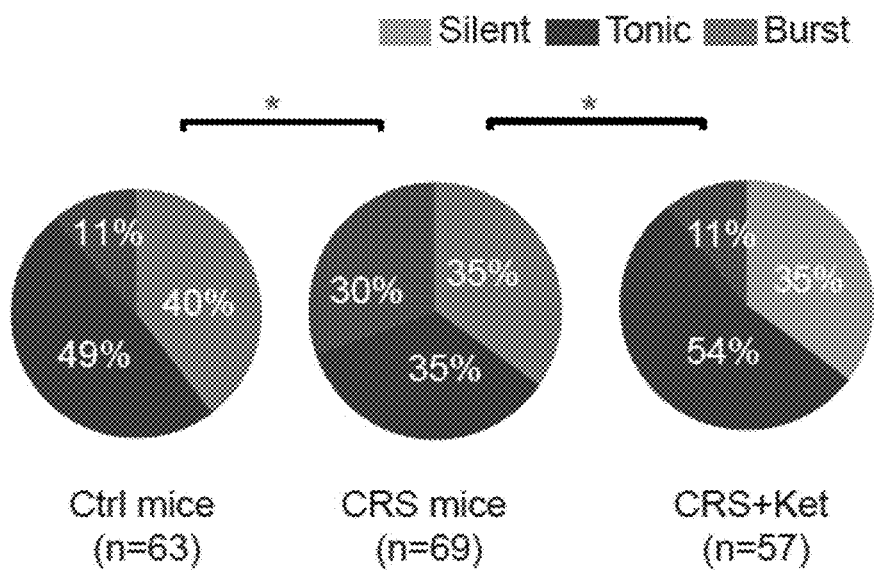
Figures 2M, 2N:
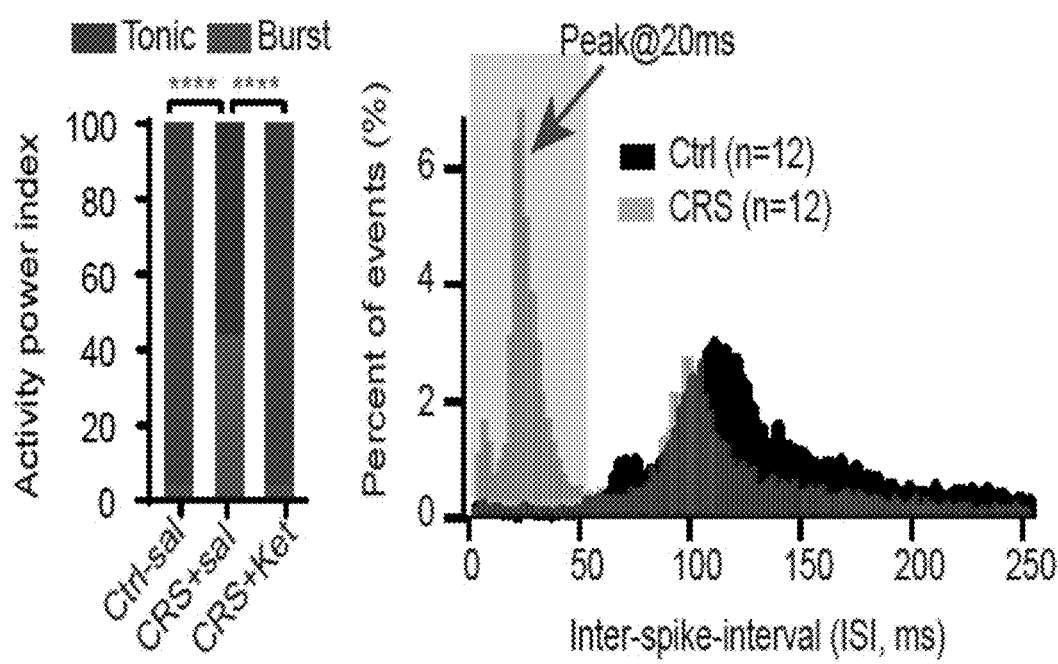

To test if enhanced bursting is universal in depression, we used a second animal model of depression, mice with chronic restraint stress (CRS). Patch clamp recording of LHb neurons in these mice revealed similar phenomena, namely, percentage of bursting cells and percentage of spikes in bursting were both dramatically increased (FIGS. 2L and 2M). ISIs of LHb neurons in CRS mice also displayed bimodal distribution and an extra peak at 20 ms (FIG. 2N).

Figure 3A:
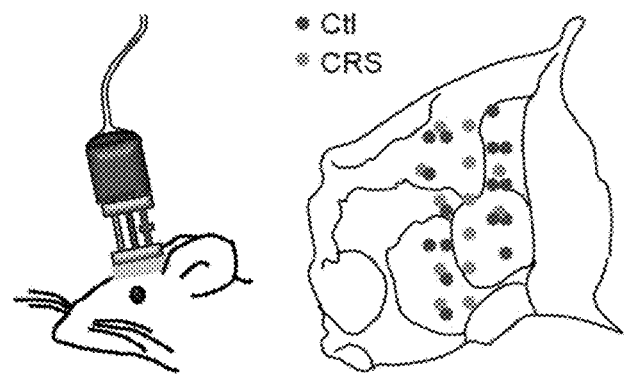
FIGS. 3A-3G show ketamine suppresses enhanced LHb bursting activity and theta-band synchronization in vivo in chronic restraint mice.
Figure 3B:
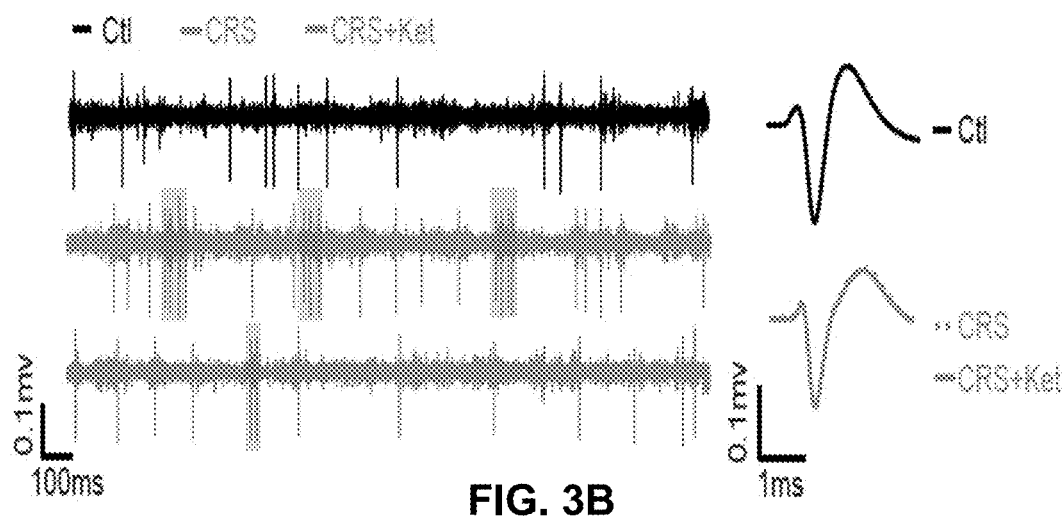
Figure 3C:
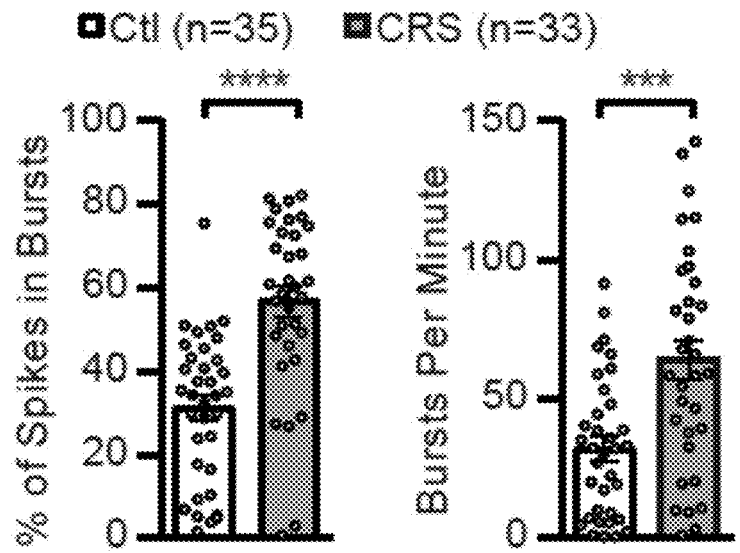
Figure 3D:
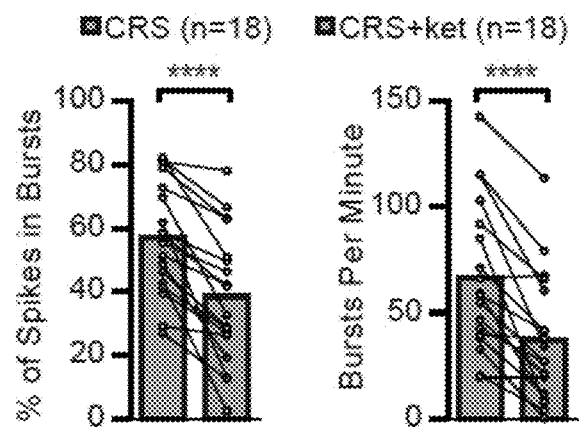
Figure 3E:
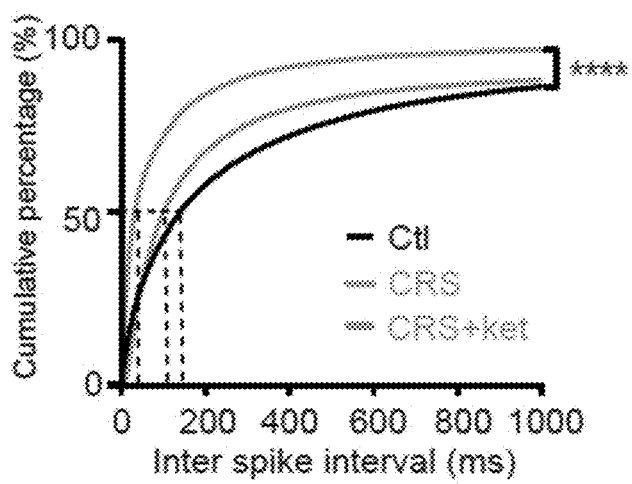

Example 4. Ketamine Suppresses Enhanced LHb Bursting Activity and Theta-Band Synchronization In Vivo in Chronic Restraint Mice To test whether burst also occurs in vivo in the LHb and whether it is bidirectionally modulated by depression state and ketamine, in vivo multi-tetrode recording was performed in the LHb of freely behaving mice (FIGS. 3A and 3B). Unlike in in vitro slice conditions where LHb neurons spike with either tonic or bursting mode, spike patterns of LHb neurons recorded in vivo switched between tonic and burst firing modes (FIG. 3B). LHb neurons from CRS mice showed a notable increase in bursting activity (FIG. 3C) but not tonic firing, compared with control naïve mice. Injection of ketamine at the antidepressant dosage (10 mg/kg, i.p., 1 h prior to recording) significantly suppressed the LHb bursting activity (FIG. 3D). The cumulative frequency distributions of ISI, which were clearly different between CRS and control mice, were significantly shifted toward control level by ketamine (FIG. 3E).

Figure 3F:
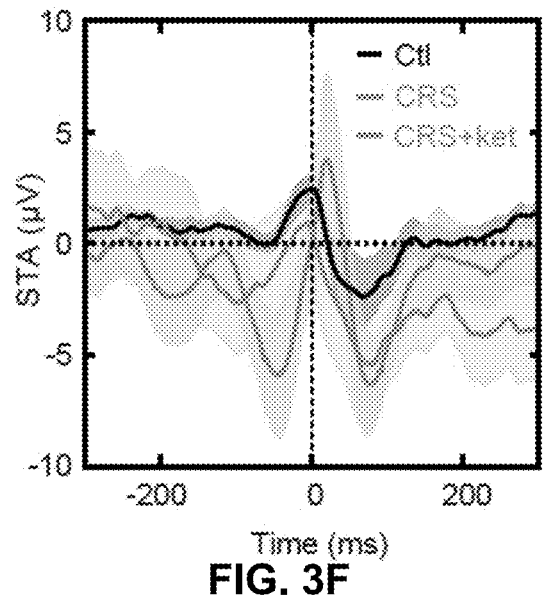
Figure 3G:
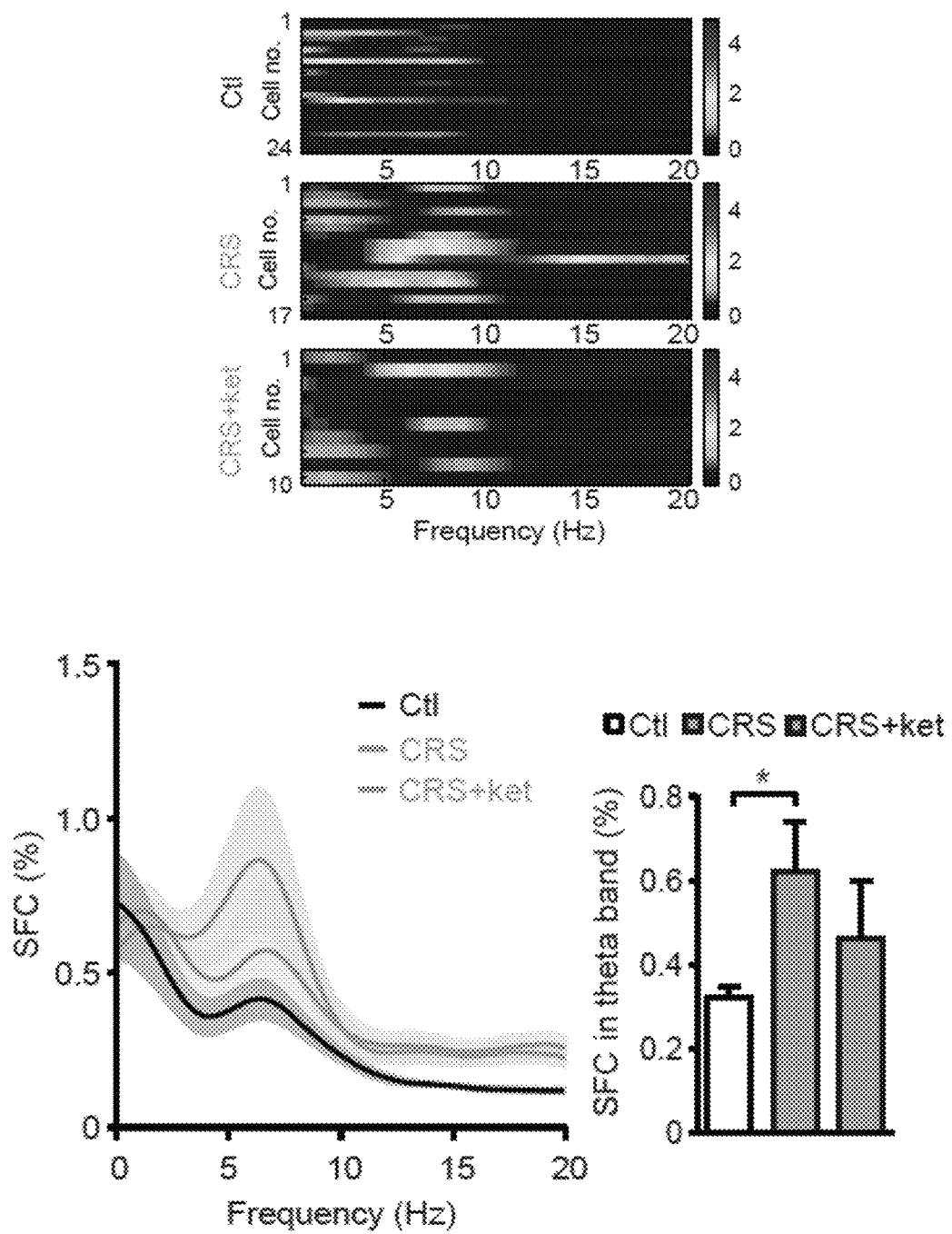

Burst firing was known to increase network synchronization. It was thus tested whether LHb network synchronization was altered in the CRS animals. It was first calculated the spike-triggered averages (STAs) of local field potential (LFP), which revealed oscillatory synchronization between spikes and LFP. In the control mice, the distribution of the power spectra of STAs was relatively flat (FIG. 3F), indicating a lack of synchronization. In the CRS mice, there emerged a dominant frequency of 7 Hz in the power spectra of STAs (FIG. 3F), indicating that spikes tended to phase-lock with LFP in the theta-band range (4-10 Hz). Consistently, CRS mice showed significantly higher spike-field coherence (SFC, reflecting normalized power spectra of STAs) in the theta band range compared with control mice (FIG. 3G). These changes in LHb network synchronization in CRS mice as reflected in STA and SFC were reversed to control level 1 hr after systemic injection of ketamine (10 mg/kg, i.p., FIG. 3G).

Together with the in vitro slice experiments, these in vivo results in freely behaving animals provide strong evidences that LHb bursting is pathologically enhanced in depression, which can be efficiently alleviated by ketamine.

Example 5. Bursts in LHb Directly Require Activation of NMDAR

Figures 4A, 4B:
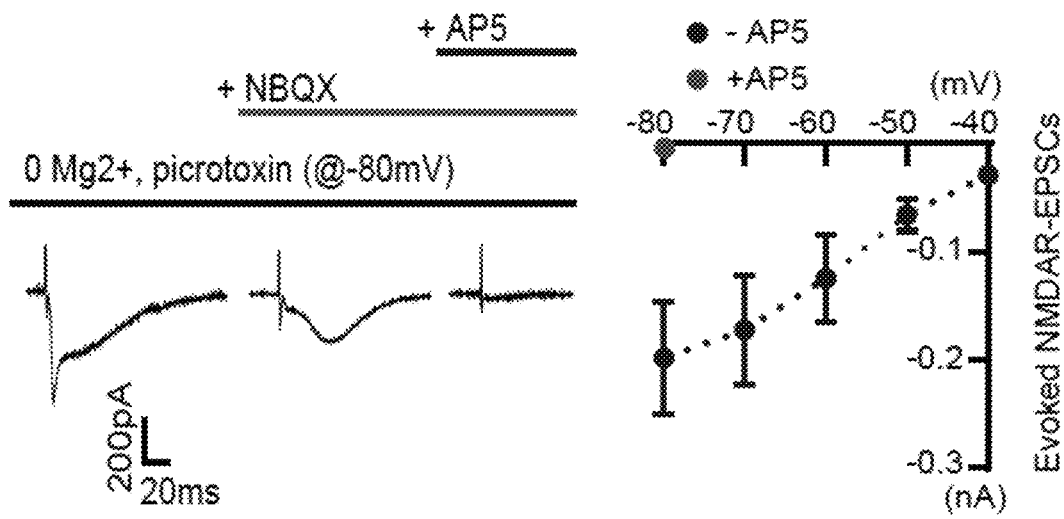
Figures 4C, 4D:
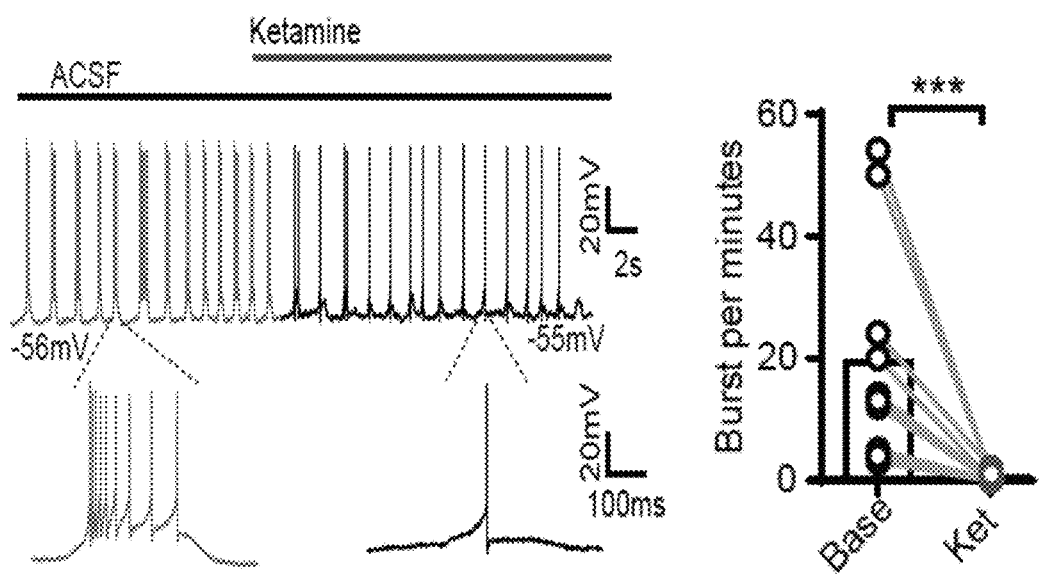

Given that NMDAR-mediated calcium influx plays a pivotal role in burst generation in several brain regions, and in light of the data that systematic injection of ketamine suppressed bursting activity (FIGS. 2A-2N and 3A-3G), it was tested if NMDARs are directly required for the bursting activity in the LHb. First to confirm that LHb expresses functional NMDARs, NMDAR-dependent excitatory post-synaptic potentials (NMDAR-EPSCs) in sagittal LHb slices was recorded by stimulating the input stria medullaris (SM) fiber in the presence of AMPA receptor (AMPAR) blocker NBQX and GABA receptor (GABAR) blocker picrotoxin and 0 $Mg^{2+}$, and isolated characteristic NMDAR-currents, which can be abolished by AP5 (FIGS. 4A and 4B). Next, ketamine (100 μM) was bath applied onto spontaneously bursting neurons recorded in the LHb brain slices, and found that ketamine almost completely eliminated spontaneous bursts (FIGS. 4C and 4D). As illustrated in FIG. 4C, within seconds after bath application of ketamine, a burst-firing LHb neuron was converted to tonic-firing mode. Similarly, bath application of a specific NMDAR antagonist AP5 (100 μM) also stopped burst-firing (FIGS. 4E and 4F). Interestingly, consistent with the behavioral effects from cannular infusion, blockade of AMPAR with NBQX (10 μM) reduced bursts, but to a much smaller extent than NMDAR blockade (FIGS. 4G and 4H).

Figure 4I:
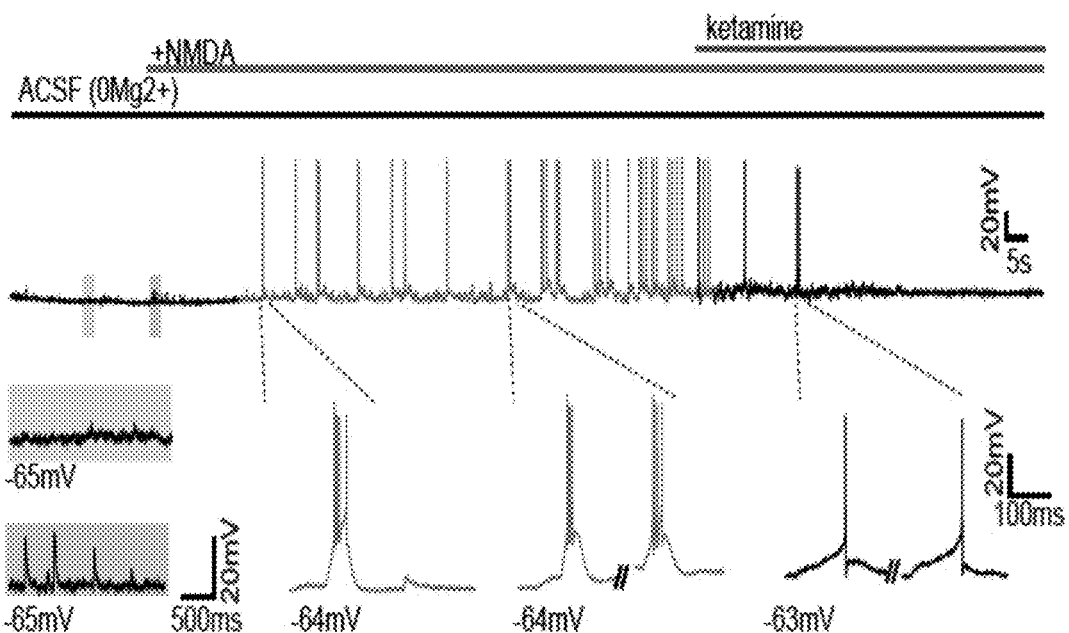
Figure 4J:
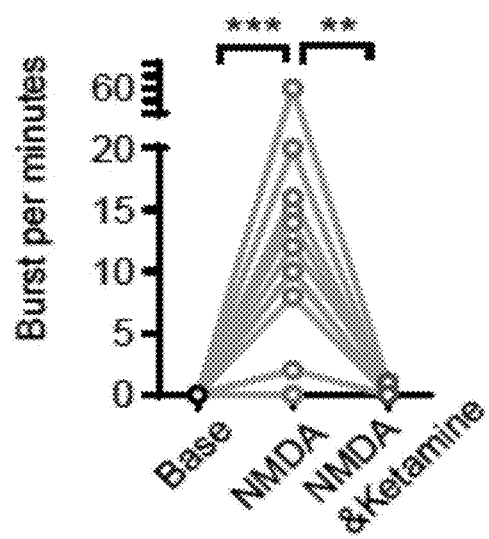

To further verify the causal link between NMDAR activity and LHb bursting, we perfused NMDA (20 μM) onto the LHb brain slice in the presence of AMPAR blocker NBQX and GABAR blocker picrotoxin and 0 $Mg^{2+}$ to activate NMDARs. NMDA application induced strong bursting activity in 10 out of 13 originally silent LHb neurons (FIGS. 4I and 4J). Again this bursting activity was blocked by additional bath application of 100 μM ketamine (FIG. 4J). FIG. 4I shows a representative example of such neurons, exhibiting dramatically enhanced EPSPs and burst firing quickly after perfusion of NMDA, and then transforming to tonic followed by silent mode after wash-in of ketamine.

Example 6. Bursts in LHb Also Depend on Hyperpolarization and Synergistic Activation of T-VSCCs Given the correlation between the RMPs and firing mode of LHb neurons, we next tested whether changing RMPs can alter the pattern of spiking activity in LHb. By applying a transient ramp-like current injection enabling RMPs to change progressively from around −80 to −40 mV (FIG. 5A), we found that in 90% of rat and 93% of mouse LHb neurons, the hyperpolarization current injection was able to evoke high frequency bursts of Aps (FIG. 5B). Similar as found in the spontaneous bursting neurons (FIG. 2G), the intra-burst frequencies of the ramp-evoked rebound bursts were positively correlated with the hyperpolarization level of membrane potential (FIG. 5C). The duration of bursts tended to decrease with more hyperpolarization (FIG. 5D). Consequently, the number of spikes in each burst, which is the product of the intra-burst frequency and burst duration, were normally distributed from −80 mV to −40 mV and peaked at −56~−60 mV (FIG. 5E), close to the average RMPs observed in spontaneous bursting LHb neurons (FIG. 2E). As current ramped into more depolarized potentials, burst firings transformed into tonic firings of single Aps, whose frequency increased with the level of depolarization (FIG. 5A).

Figure 5F:
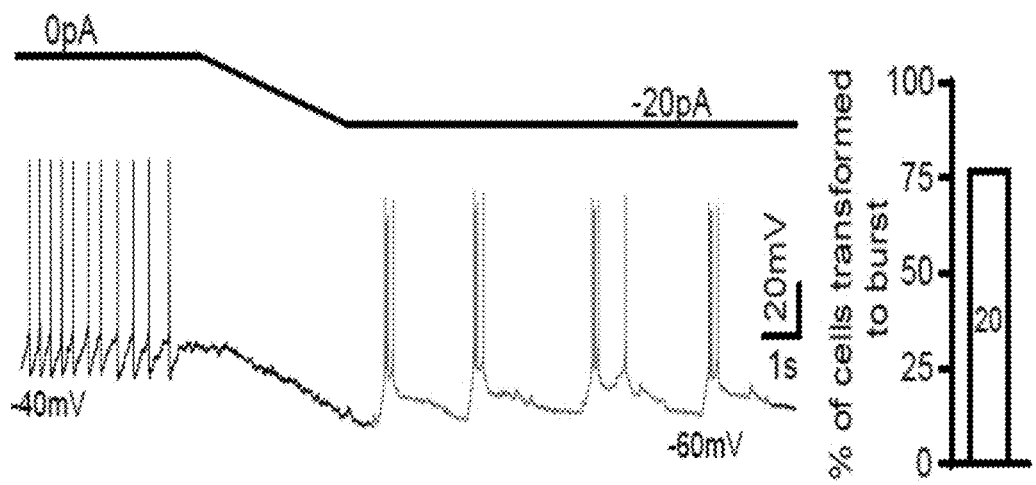
Figure 5G:
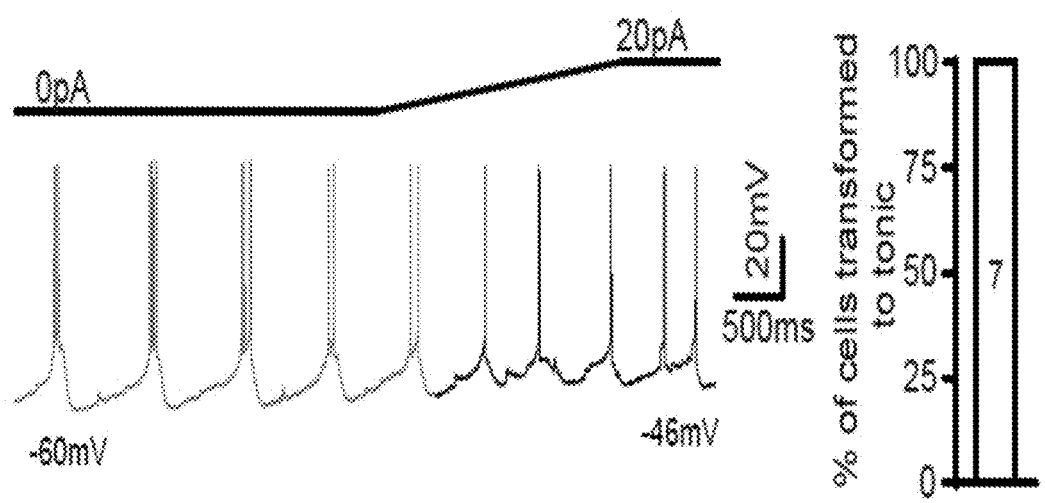

This voltage-dependent transition of firing mode also occurred in spontaneously-spiking LHb neurons. By delivering a hyperpolarizing current injection (−10~−20 pA), 75% of originally tonic-firing neurons could be transformed to burst-firing mode (FIG. 5F). Vice versa, with a depolarizing current injection (10~20 pA), 100% of originally bursting neurons could be transformed to tonic firing mode (FIG. 5G). These results indicated that, within the very same LHb neuron, the activity pattern can be transformed from tonic to burst firing, or vice versa, depending on the membrane potential.

Figure 5H:
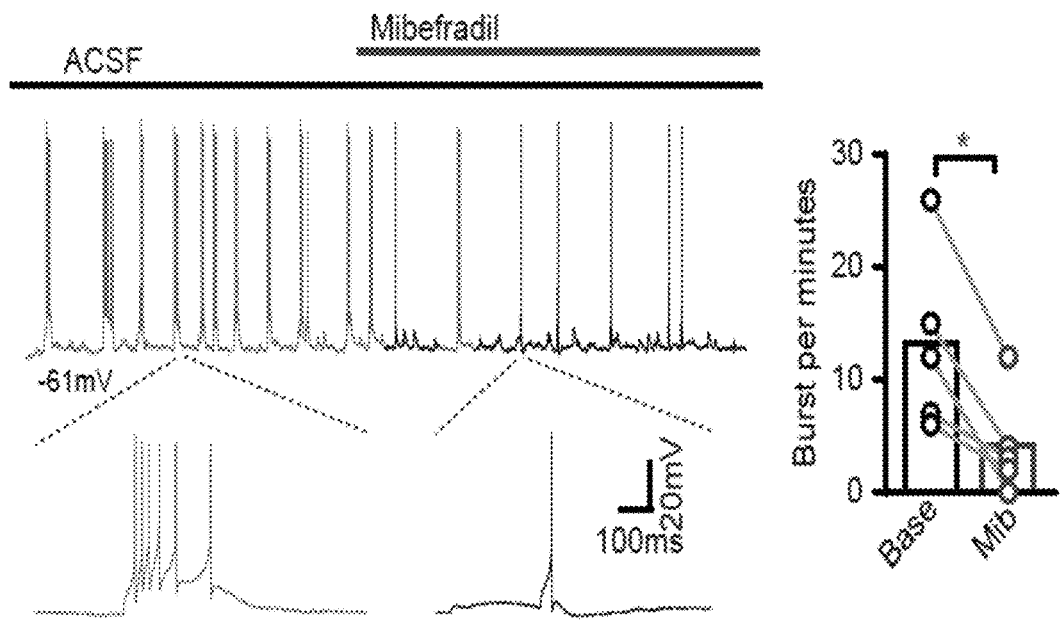
Figure 5I:
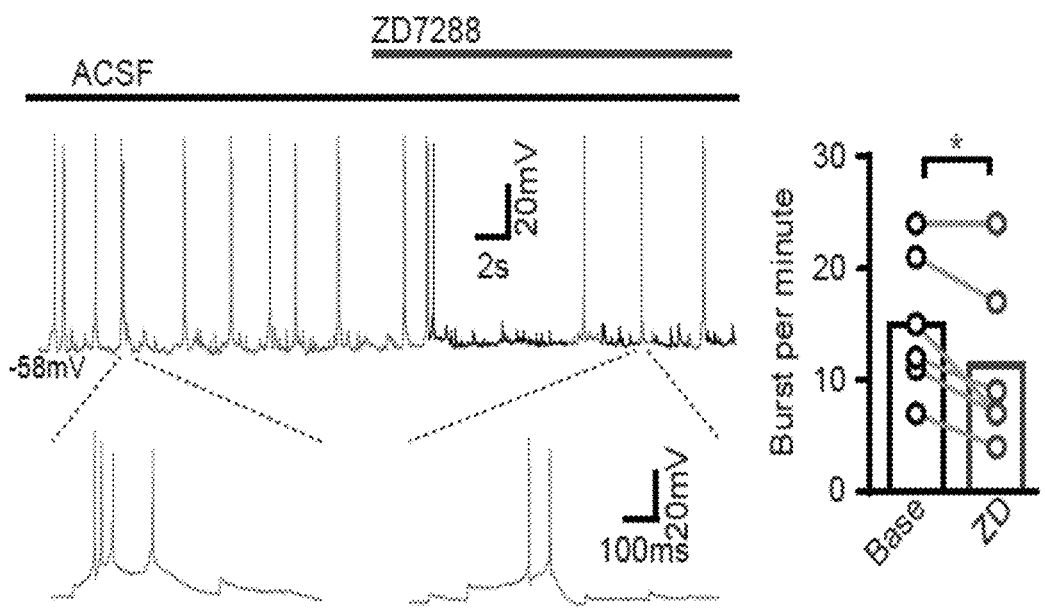

Since NMDAR alone does not explain the voltage-dependence of LHb bursts, we searched for more ion channels involved. The T-type Voltage Sensitive Calcium Channels (T-VSCCs, including Cav3.1, 3.2, 3.3) are known to have pacemaker activity and are expressed in LHb neurons. Unlike other types of voltage sensitive calcium channels, T-VSCCs are inactivated quickly after opening at depolarized membrane potentials, but can be de-inactivated to initiate burst firings when the membrane potential is hyperpolarized for longer than 100 ms. Bath application of mibefradil (10 µM), onto the LHb brain slices effectively decreased the bursting probability and reduced the amplitude of plateau potential of spontaneous bursts (FIG. 5H). ZD7288 (50 µM), an antagonist of another pacemaker channel (hyperpolarization-activated cyclic nucleotide-gated (HCN) channel), had a significant but much smaller effect on bursts than mibefradil (P=0.018, FIG. 5I).

Figure 5J:
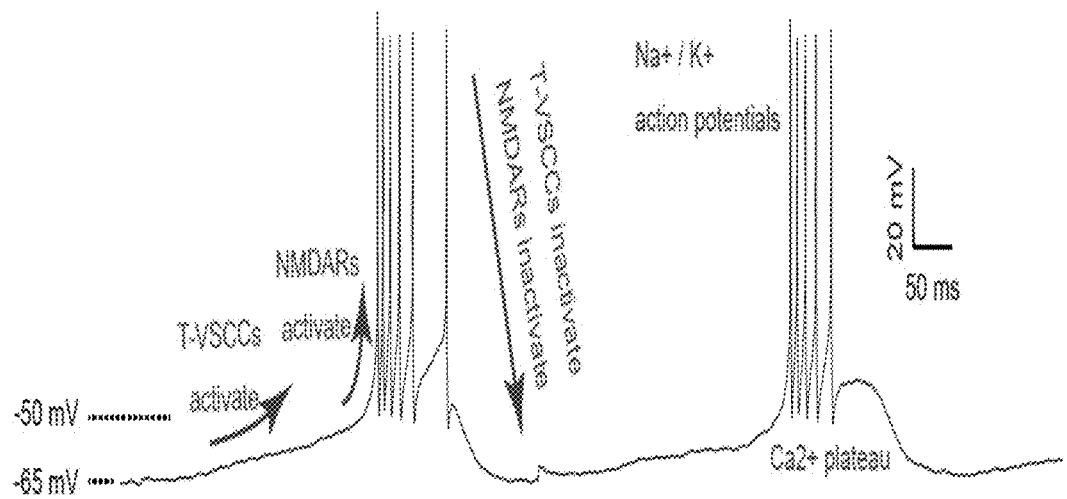

To understand how NMDARs and T-VSCCs work synergistically to mediate LHb burst firing, we constructed a minimal biophysical model incorporating these two channels (FIG. 5J). Burst generation was successfully modeled and depended critically on the ionic currents of T-VSCC ($I_T$) and NMDAR ($I_{NMDA}$): hyperpolarization of neurons to membrane potentials negative to −55 mV slowly de-inactivates T-VSCC. $I_T$ continues to grow as the de-inactivated T-VSCCs increase, leading to a transient Ca plateau potential. The Ca plateau helps remove the magnesium blockade of NMDARs while T-VSCC inactivates rapidly during the depolarization. After the $Ca^{2+}$ plateau reaches approximately −45 mV, $I_{NMDA}$ dominants the driving force to further depolarize RMP to the threshold for Na spike generation. The falling back to RMP below −55 mV again de-inactivates $I_T$ and results in the intrinsic propensity of LHb neurons to generate the next cycle of burst (FIG. 5J).

Example 7. Local LHb Blockade of T-VSCCs is Rapidly Anti-Depressive

Figures 6A, 6B:
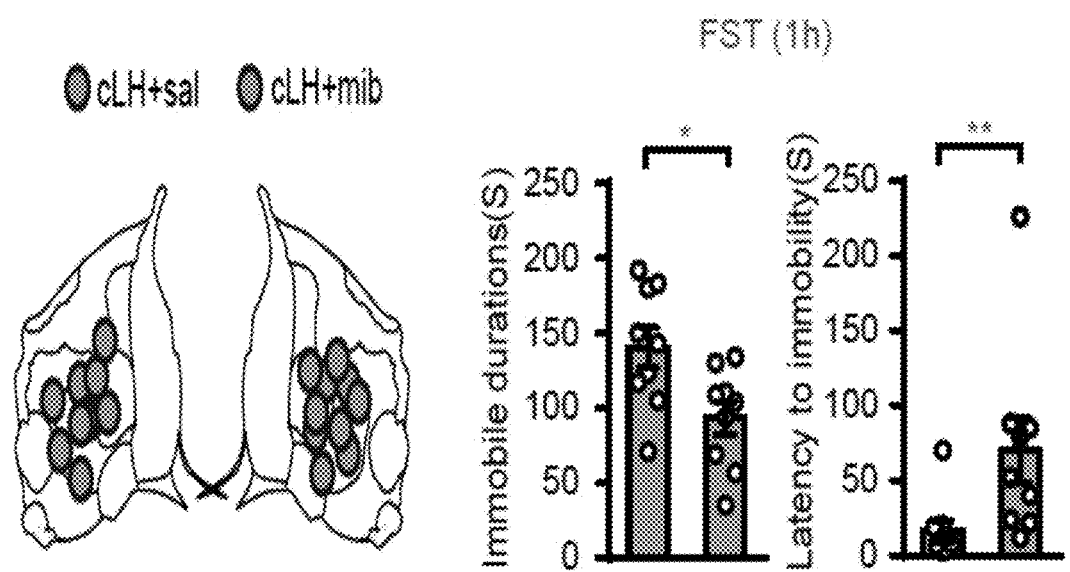

The above results predict that drugs blocking T-VSCCs may be also antidepressant. To test that, we performed bilateral infusion of a selective T-VSCC blocker, mibefradil (10 nmol, 1 ul each side), in the LHb of cLH rats through dual guide cannulae (FIG. 6A). mibefradil infusion quickly rescued the depressive-like behaviors, including the immobility in the FST (FIG. 6B) and the anhedonia in the SPT (FIG. 6C) 1 hr after infusion.

Figure 7B:
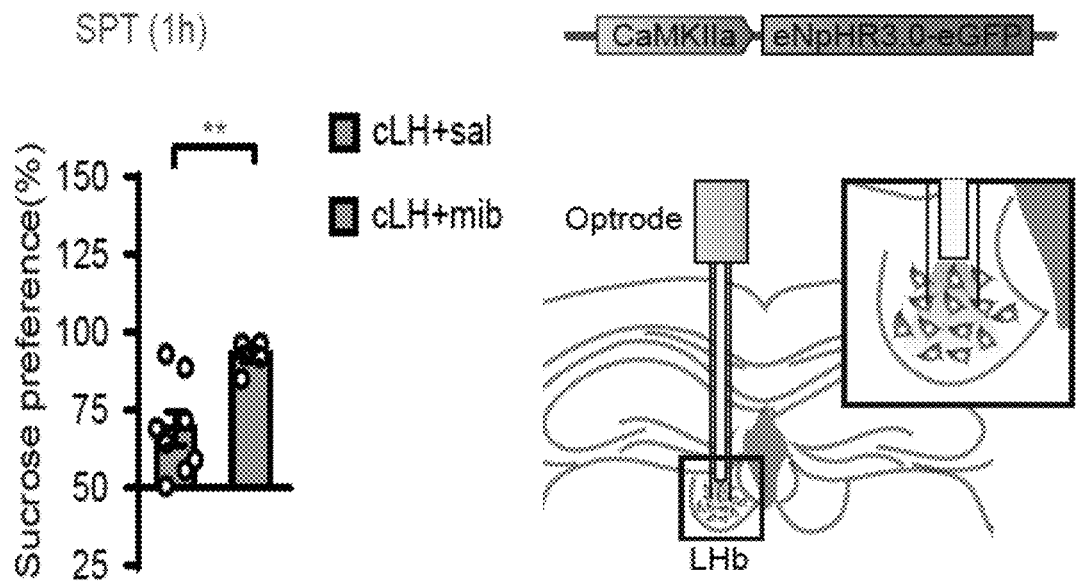
Figure 7B:
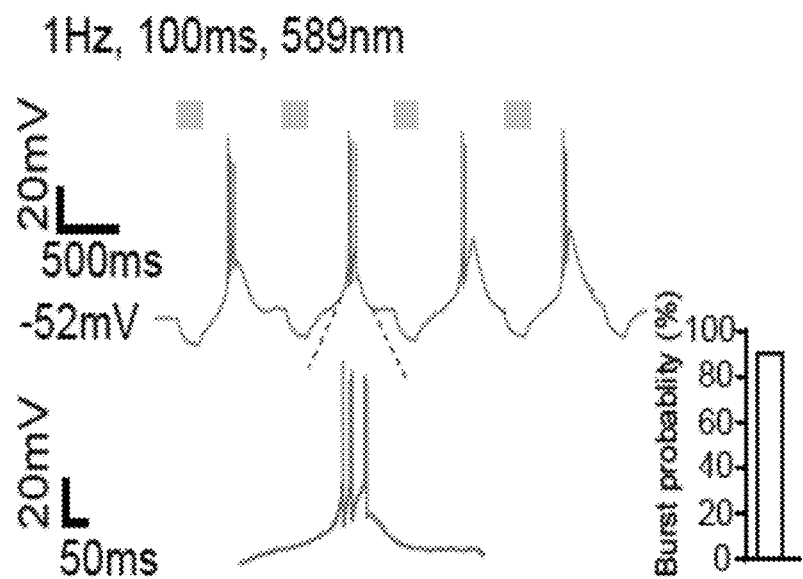

Example 8. NpHR-Induced Rebound Burst Drives Behavioral Aversion and Depressive-Like Symptoms Based on the observation that a hyperpolarization ramp current could induce burst firing in the LHb (FIGS. 5A and 5B), a protocol employing a transient (100 ms) hyperpolarization current injection was devised, which induced rebound bursts in the LHb brain slices with 100% success rate. We thus used an inhibitory opsin, eNpHR3.0 (an enhanced variant of halorhodopsin) to drive rebound bursts in the LHb (FIG. 7A). 1 Hz, 100 ms of 589 nm yellow light pulses reliably elicited robust rebound bursts in in vitro slice recording with a high intra-burst frequency and 90% success rate (FIG. 7B), as well as in in vivo as revealed by optrode recording (FIGS. 7C and 7D). The intra-burst frequency and intra-burst number of spikes produced by this rebound burst protocol were comparable to those detected in depressed CRS mice (FIG. 7E).

Figure 7F:
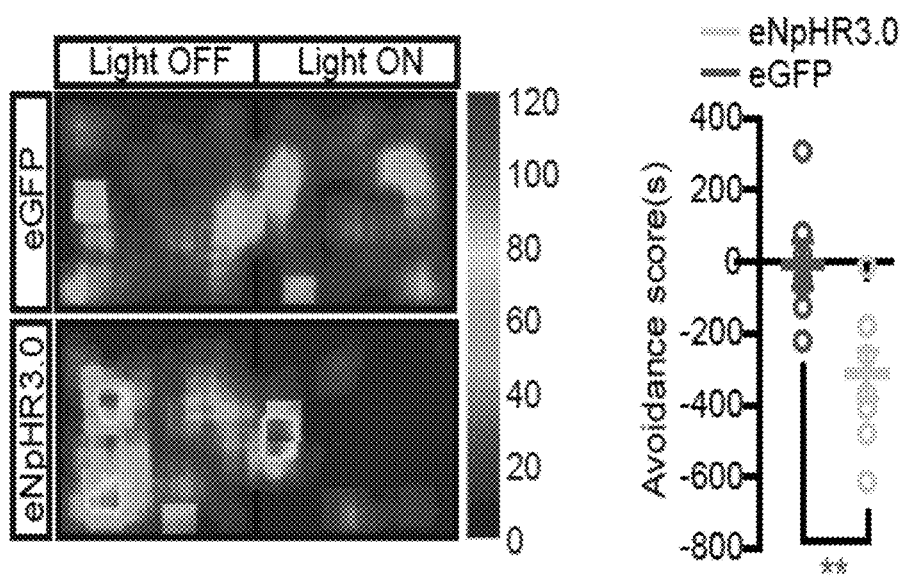
Figures 7G, 7H:
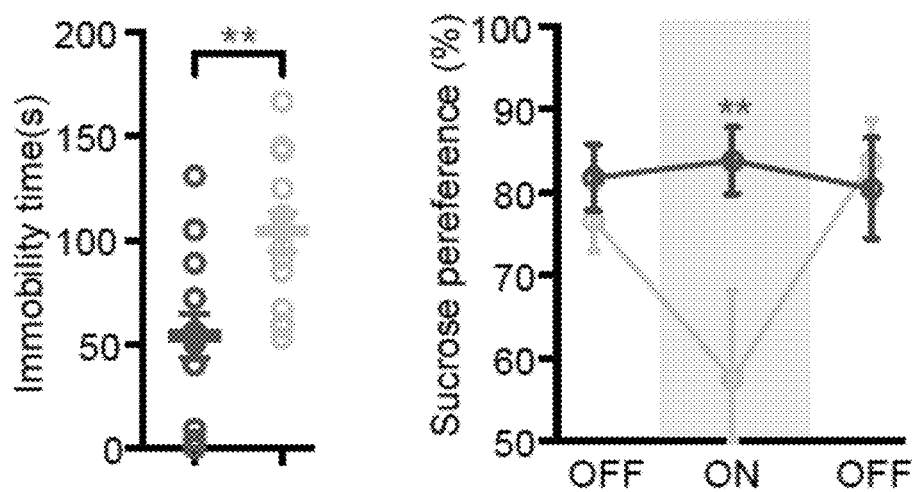

It was then tested whether the rebound bursts in the LHb could acutely drive aversion and depressive-like symptoms in freely behaving mice. In the real-time place aversion (RTPA) assay, 1 Hz yellow light photostimulation significantly reduced the time spent in the light-paired chamber in mice injected with AAV-eNpHR3.0 but not those with AAV-eGFP (FIG. 7F). Furthermore, 1 Hz yellow light photostimulation significantly increased the immobility (FIG. 7G) and decreased sucrose preference (FIG. 7H) in the eNpHR3.0 group.

Figure 8A:
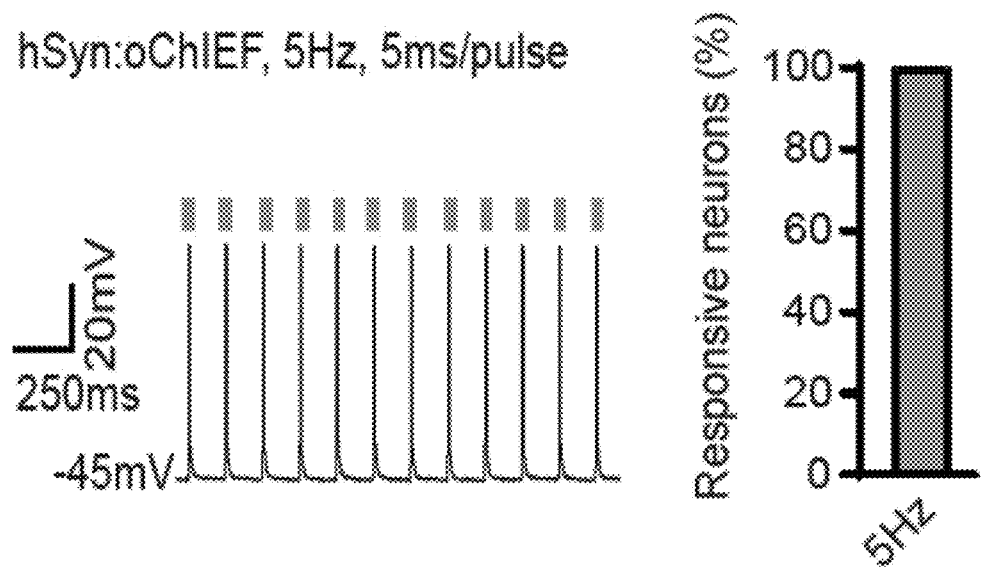
FIGS. 8A-8C show stimulation yielded the same overall firing rate as the rebound burst protocol do not cause depressive-like phenotypes.
Figures 8B, 8C:
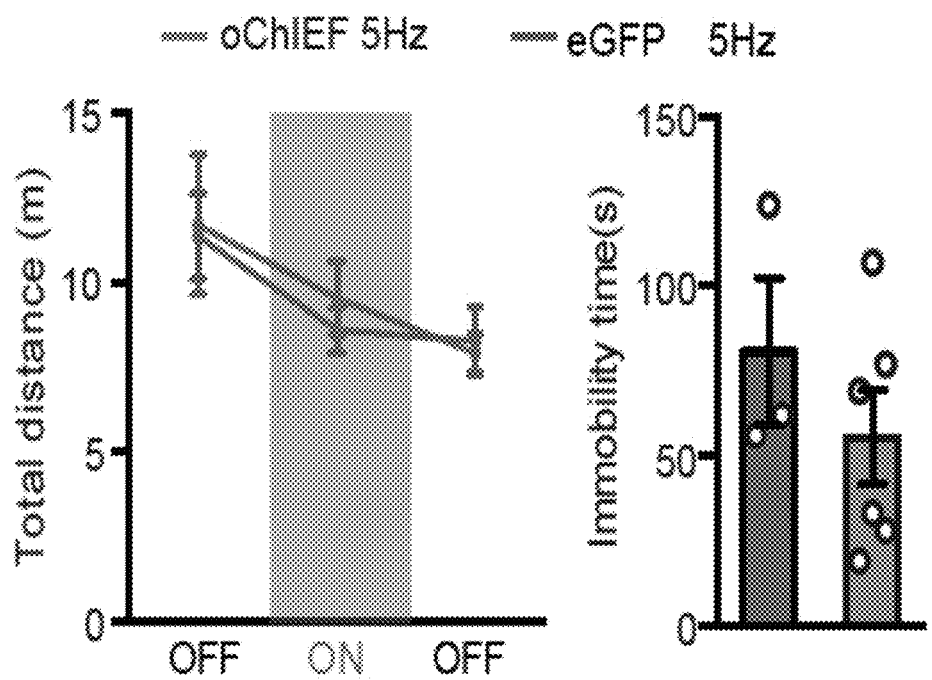

To prove that it is the bursting firing mode but not the general increase in firing rate that is important for the induction of depressive-like behaviors, we applied a stimulation protocol (5 Hz on AAV-oChIEF injected mice) that yields the same overall firing rate as the rebound burst protocol (FIG. 8A). This did not cause depressive-like phenotypes (FIGS. 8B and 8C).

Collectively, these results indicated that bursting activity in the LHb can acutely drive depressive-like state.

Figure 9:
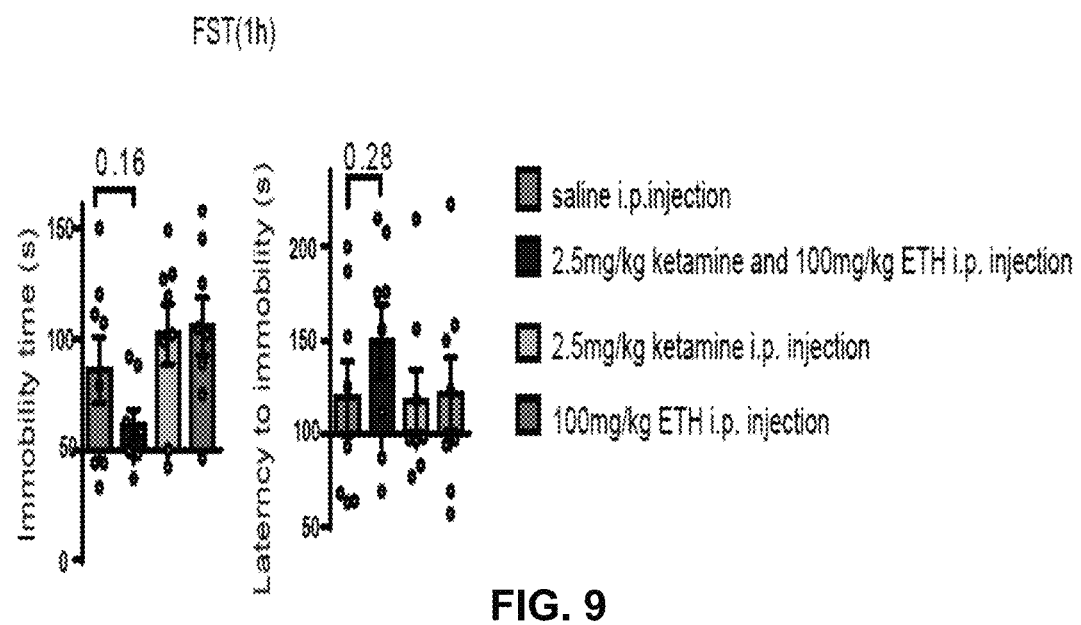
FIG. 9 shows antidepressant-like effect of low dose ketamine and ethosuximide co-treatment in mice. Low dose ketamine (2.5 mg/kg) or ethosuximide (ETH, 100 mg/kg) is ineffective in the mouse FST. Co-treatment with subeffective doses of both drugs has an antidepressant-like effect.
Figure 10A:
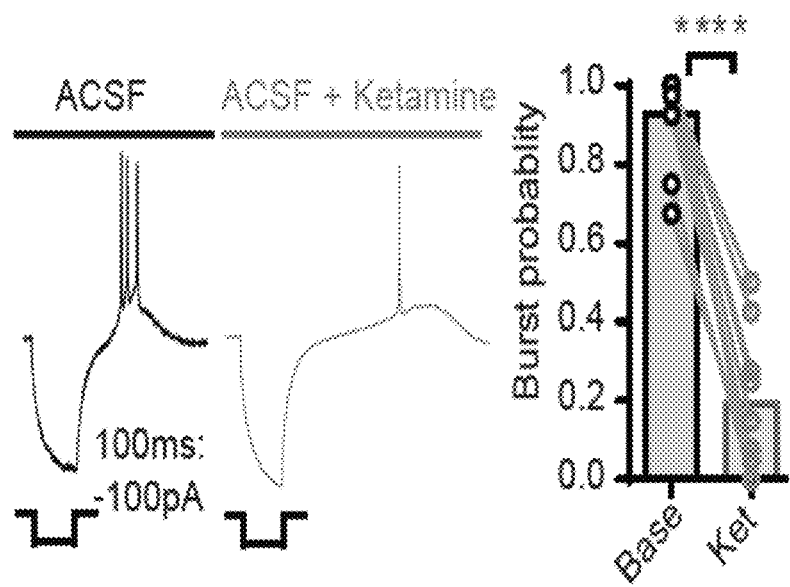
FIGS. 10A-10E. Pharmacological manipulations of hyperpolarization—triggered rebound bursts in LHb.
Figure 10B:
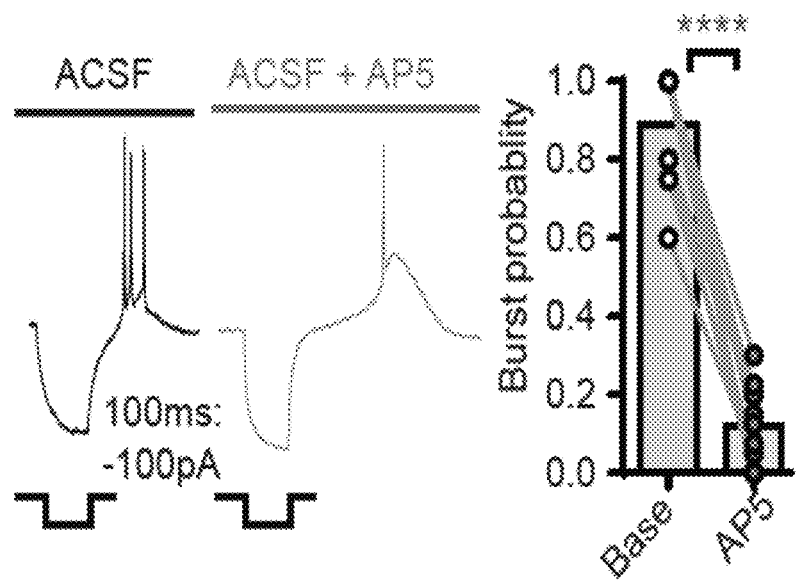
Figure 10C:
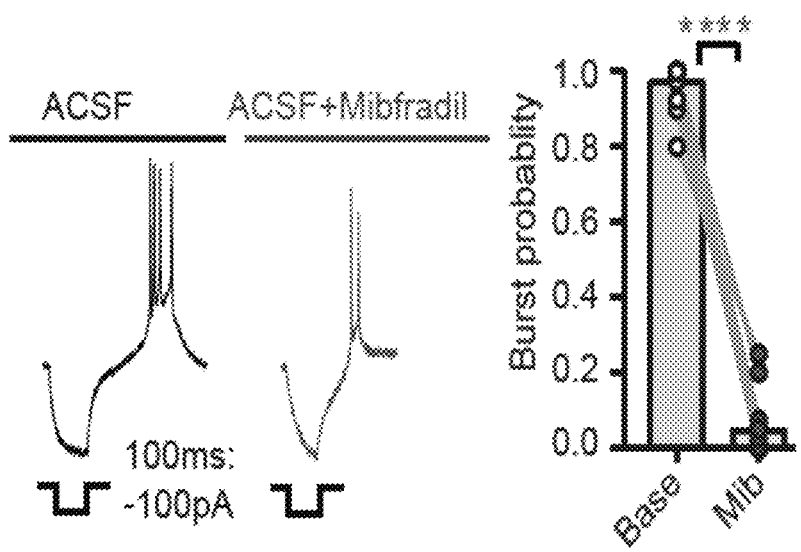
Figure 10D:
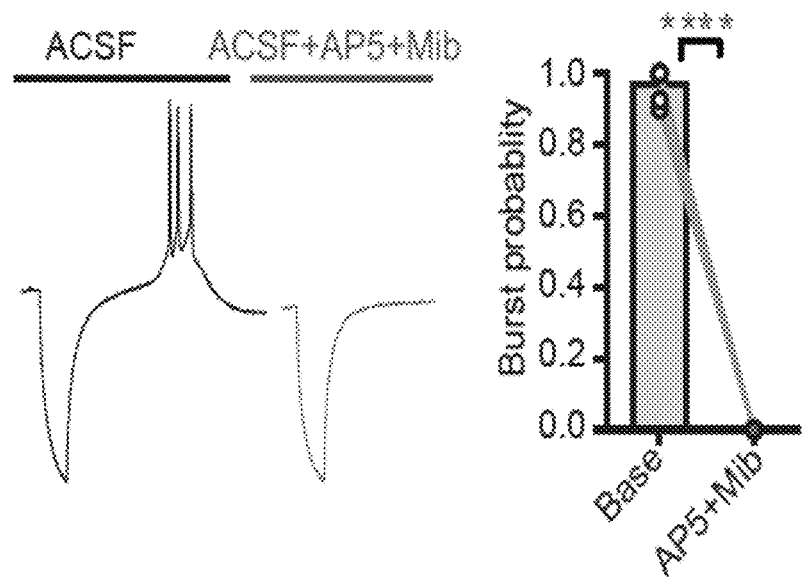
Figure 10E:
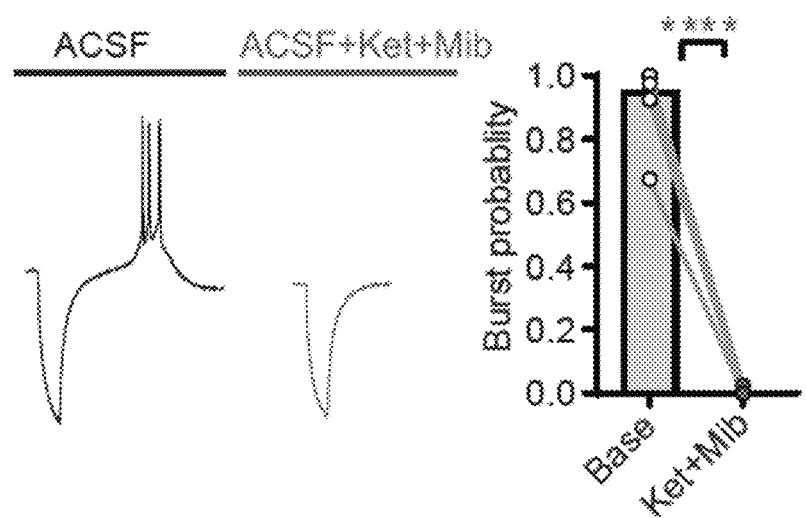

Example 9. Co-Administration of Subeffective Antidepressant Doses of NMDAR Antagonist and T-VSCC Antagonist has an Antidepressant-Like Effect Low dose ketamine (one of the NMDAR antagonists, 2.5 mg/kg) or ethosuximide (ETH, one of the T-VSCC antagonists, 100 mg/kg) is ineffective in the forced swim test in C56BL/6 mice 1 hour after drug administration (i.p.) (FIG. 9). In co-administration of 2.5 mg/kg of ketamine and 100 mg/kg ethosuximide, as subeffective antidepressant doses of either drug, the immobility time was reduced and latency to immobility was increased compared to control group (FIG. 9). Hence, Co-administration of subeffective antidepressant doses of ketamine and ethosuximide could an antidepressant-like effect.

These above in vivo experiments suggest that administering an NMDA receptor inhibitor at a dosage lower than its working dosage in combination with administering a T-VSCC receptor inhibitor at a dosage lower than working dosage, could be effective in generating a significant anti-depression effect.

Example 10. Pharmacological Manipulations of Hyperpolarization-Triggered Rebound Bursts in LHb To further test the effect of NMDAR inhibitors combined with T-VSCC inhibitors on the induction of burst firing, the effects on inducing burst firing by NMDAR inhibitors and T-VSCC inhibitors alone or in combination were tested.

Based on the observation that a hyperpolarization ramp current could induce burst firing in the LHb, a protocol was devised employing a transient (100 ms) hyperpolarization current injection, which induced rebound bursts in the LHb brain slices with 100% success rate (FIGS. 10A-10E). As seen, −100 pA hyperpolarization current was injected into the lateral habenular neurons for 100 ms, which made the neurons hyperpolarized, and the hyperpolarization state induced burst firings of the lateral habenular neurons.

When the lateral habenular slices were perfused with ketamine (100 µM, FIG. 10A), AP5 (100 µM, FIG. 10B) or mibefradil (10 µM, FIG. 10C), the probability of neuron hyperpolarization-induced burst was partially reduced to 0.19, 0.12 and 0.05, respectively. When AP5 (100 µM) was administered in combination with mibefradil (10 µM, FIG. 10D) or ketamine (100 µM) was administered in combination with mibefradil (10 µM, FIG. 10E), the probability of neuron hyperpolarization—induced burst in both tests were further reduced to almost zero, which means a complete blocking of the hyperpolarization-induced burst.

Thus in other words, the hyperpolarization-induced rebound bursts can be partially inhibited by ketamine (100 µM, FIG. 10A), AP5 (100 µM, FIG. 10B), or mibefradil (10 µM, FIG. 10C), but can be almost fully blocked by mibefradil (10 µM) in combination with ketamine (100 µM, FIG. 10E) or AP5 (100 µM, FIG. 10D), indicating that the combination of NMDAR antagonists and T-VSCC antagonists has a strong synergy in modulating the hyperpolarization-induced rebound bursts.

Collectively, these above in vitro experiments demonstrate that a combination of a low dose of an NMDA receptor inhibitor that is lower than the effective dose when administered alone and a low dose of a T-VSCC receptor inhibitor that is also lower than the effective dose when administered alone can produce a much more pronounced and significant antidepressant effect. It is also noteworthy that since the lower than effective doses of the NMDA receptor inhibitor and the T-VSCC receptor inhibitor are administered, there is potentially another benefit for a reduced side effect for both drugs.

Unless otherwise indicated, the practice of the present disclosure will employ common technologies of organic chemistry, polymer chemistry, biotechnology, and the like. It is apparently that in addition to the above description and examples than as specifically described, the present disclosure can also be achieved in other ways. Other aspects within the scope of the disclosure and improvement of the present disclosure will be apparent to the ordinary skilled in the art. According to the teachings of the present disclosure, many modifications and variations are possible, and therefore it is within the scope of the present disclosure.

Unless otherwise indicated herein, the temperature unit "degrees" refers to Celsius degrees, namely ° C.

All references that have been referred to in the present application are incorporated by reference in their entirety.

REFERENCES

1. GraphPad Statistics Guide: http://www.graphpad.com/guides/prism/7/statistics/index.htm.
2. Li et al. Nature 470, 535-539, 2011.
3. Li et al., Science 341, 1016-1020, 2013.
4. Schulz et al., Neurobiol Learn Mem 93, 291, February 2010.
5. Yang et al. Nature 554, 317-322, 2018.

The invention claimed is:

1. A method for treating a depression in a subject, comprising:
    examining whether neurons of a lateral habenula (LHb) of the subject have an increased burst firing; and
    if so, administering to the subject a pharmaceutical composition that inhibits the burst firing in the LHb of the subject, wherein the pharmaceutical composition comprises at least one of an N-methyl-D-aspartate receptor (NMDAR) inhibitor or a T-type calcium channel inhibitor.

2. The method of claim 1, wherein the administering to the subject a pharmaceutical composition that inhibits the burst firing in the LHb of the subject comprises:
    administering the pharmaceutical composition locally to the LHb of the subject.

3. The method of claim 1, wherein the administering to the subject a pharmaceutical composition that inhibits the burst firing in the lateral habenula of the subject comprises:
    administering the pharmaceutical composition systemically to the subject.

4. The method of claim 1, wherein the pharmaceutical composition comprises an N-methyl-D-aspartate receptor (NMDAR) inhibitor.

5. The method of claim 4, wherein the NMDAR inhibitor is a competitive NMDA receptor inhibitor, a non-competitive NMDA receptor inhibitor, an uncompetitive NMDA receptor channel blocker, or a glycine binding site inhibitor.

6. The method of claim 1, wherein the pharmaceutical composition comprises a T-type calcium channel inhibitor.

7. The method of claim 6, wherein the T-type calcium channel inhibitor is a succinimide, a hydantoin, zonisamide, sodium valproate, phenytoin, mibefradil, sipatrigine, a piperazine analogue, a piperidine analogue, TTA-P1, TTA-P2, quinazolinone, pimozide, trimethadione, dimethadione, TTA-Q4, or ML218.

8. The method of claim 1, wherein the pharmaceutical composition comprises an N-methyl-D-aspartate receptor (NMDAR) inhibitor and a T-type calcium channel inhibitor.

9. The method of claim 8, wherein a dose of one or both of the NMDA receptor inhibitor and the T-type calcium channel inhibitor is lower than an effective dose thereof when administered alone.

10. The method of claim 1, wherein the pharmaceutical composition does not inhibit tonic firing in the lateral habenula of the subject.

11. The method of claim 1, wherein the pharmaceutical composition allows for fast-acting treatment of the depression.

* * * * *